US011964114B2

(12) United States Patent
Matlock et al.

(10) Patent No.: US 11,964,114 B2
(45) Date of Patent: Apr. 23, 2024

(54) SHAFT DEFLECTION CONTROL ASSEMBLY FOR ENT GUIDE INSTRUMENT

(71) Applicant: Acclarent, Inc., Irvine, CA (US)

(72) Inventors: George L. Matlock, Laguna Hills, CA (US); Jetmir Palushi, Irvine, CA (US); Behnam Amin, Mission Viejo, CA (US); Karthick Ramyan Mohan, Irvine, CA (US); Krishna M. Rajan, Bangalore (IN)

(73) Assignee: Acclarent, Inc., Irvine, CA (US)

( * ) Notice: Subject to any disclaimer, the term of this patent is extended or adjusted under 35 U.S.C. 154(b) by 296 days.

(21) Appl. No.: 17/239,761

(22) Filed: Apr. 26, 2021

(65) Prior Publication Data

US 2021/0361912 A1 Nov. 25, 2021

Related U.S. Application Data

(60) Provisional application No. 63/028,609, filed on May 22, 2020.

(51) Int. Cl.
*A61M 25/01* (2006.01)
*A61B 17/00* (2006.01)
(Continued)

(52) U.S. Cl.
CPC ... *A61M 25/0136* (2013.01); *A61B 17/00234* (2013.01); *A61B 17/24* (2013.01);
(Continued)

(58) Field of Classification Search
CPC ... A61B 1/233; A61B 17/00234; A61B 17/24; A61B 2017/00115; A61B 2017/00309;
(Continued)

(56) References Cited

U.S. PATENT DOCUMENTS

| 2,926,426 A | 3/1960 | Lury |
| 5,325,845 A | 7/1994 | Adair |

(Continued)

FOREIGN PATENT DOCUMENTS

| CN | 107485360 A | 12/2017 |
| EP | 0605796 B1 | 8/2003 |
| EP | 1905376 B1 | 9/2010 |

OTHER PUBLICATIONS

International Search Report and Written Opinion dated Nov. 4, 2021, for International Application No. PCT/IB2021/053954, 18 pages.

*Primary Examiner* — Mohamed G Gabr
(74) *Attorney, Agent, or Firm* — Frost Brown Todd LLP

(57) ABSTRACT

An apparatus includes a body, a shaft assembly, and a deflection actuation assembly. The shaft defines a longitudinal axis and includes a flexible distal portion. The deflection actuation assembly includes a first rotary actuator, a translatable actuation member, and a resilient member. The translatable actuation member extends through the shaft assembly and is operatively coupled with the first rotary actuator and the flexible distal portion of the shaft assembly. The first rotary actuator is rotatable by a rotational force to thereby drive the translatable actuation member longitudinally. The resilient member is positioned between the first rotary actuator and the body and is configured to apply a friction force between the first rotary actuator and the body. The friction force is operable to increase the rotational force required to rotate the first rotary actuator.

20 Claims, 18 Drawing Sheets

(51) Int. Cl.
*A61B 17/24* (2006.01)
*A61B 34/00* (2016.01)
*A61M 29/02* (2006.01)

(52) U.S. Cl.
CPC .............. *A61B 34/76* (2016.02); *A61M 29/02* (2013.01); *A61B 2017/00115* (2013.01); *A61B 2017/00314* (2013.01); *A61B 2017/00323* (2013.01); *A61M 2029/025* (2013.01)

(58) Field of Classification Search
CPC ........... A61B 2017/00314; A61B 2017/00323; A61B 34/76; A61M 2029/025; A61M 25/0136; A61M 25/0147; A61M 29/02
See application file for complete search history.

(56) References Cited

U.S. PATENT DOCUMENTS

| | | | |
|---|---|---|---|
| 5,904,667 A | 5/1999 | Falwell | |
| 5,989,232 A | 11/1999 | Yoon | |
| 6,533,772 B1 * | 3/2003 | Sherts | A61M 25/0136 279/42 |
| 6,571,131 B1 | 5/2003 | Nguyen | |
| 8,771,203 B2 | 7/2014 | Jen et al. | |
| 8,845,521 B2 | 9/2014 | Maruyama | |
| 9,155,492 B2 | 10/2015 | Jenkins et al. | |
| 9,307,891 B2 | 4/2016 | Carter et al. | |
| 9,693,779 B2 | 7/2017 | Wolfe | |
| 9,956,366 B2 | 5/2018 | Kirkpatrick et al. | |
| 10,039,436 B2 | 8/2018 | Tah et al. | |
| 10,213,251 B2 | 2/2019 | Otsuka et al. | |
| 10,561,370 B2 | 2/2020 | Salazar et al. | |
| 10,874,839 B2 | 12/2020 | Matlock et al. | |
| 2007/0032759 A1 | 2/2007 | Falwell et al. | |
| 2008/0027415 A1 * | 1/2008 | Isaacson | A61M 25/0097 604/539 |
| 2008/0275483 A1 | 11/2008 | Makower et al. | |
| 2010/0249773 A1 * | 9/2010 | Clark | A61B 34/74 606/41 |
| 2010/0274188 A1 | 10/2010 | Chang et al. | |
| 2011/0004057 A1 | 1/2011 | Goldfarb et al. | |
| 2012/0053595 A1 | 3/2012 | Nakao | |
| 2013/0131593 A1 | 5/2013 | Selkee | |
| 2013/0158379 A1 | 6/2013 | Selkee | |
| 2013/0274715 A1 | 10/2013 | Chan et al. | |
| 2014/0364725 A1 | 12/2014 | Makower | |
| 2017/0000990 A1 | 1/2017 | Gerrans et al. | |
| 2018/0050195 A1 * | 2/2018 | Knippel | A61N 1/057 |
| 2018/0311472 A1 | 11/2018 | Matlock et al. | |
| 2019/0008363 A1 | 1/2019 | Walish et al. | |
| 2019/0015179 A1 | 1/2019 | Kuo | |
| 2019/0015646 A1 | 1/2019 | Matlock et al. | |
| 2019/0083748 A1 | 3/2019 | Khuu et al. | |
| 2019/0192324 A1 | 6/2019 | Moore et al. | |
| 2019/0365204 A1 | 12/2019 | Lang et al. | |
| 2020/0061340 A1 | 2/2020 | Mixter et al. | |
| 2020/0078559 A1 | 3/2020 | Guo et al. | |

* cited by examiner

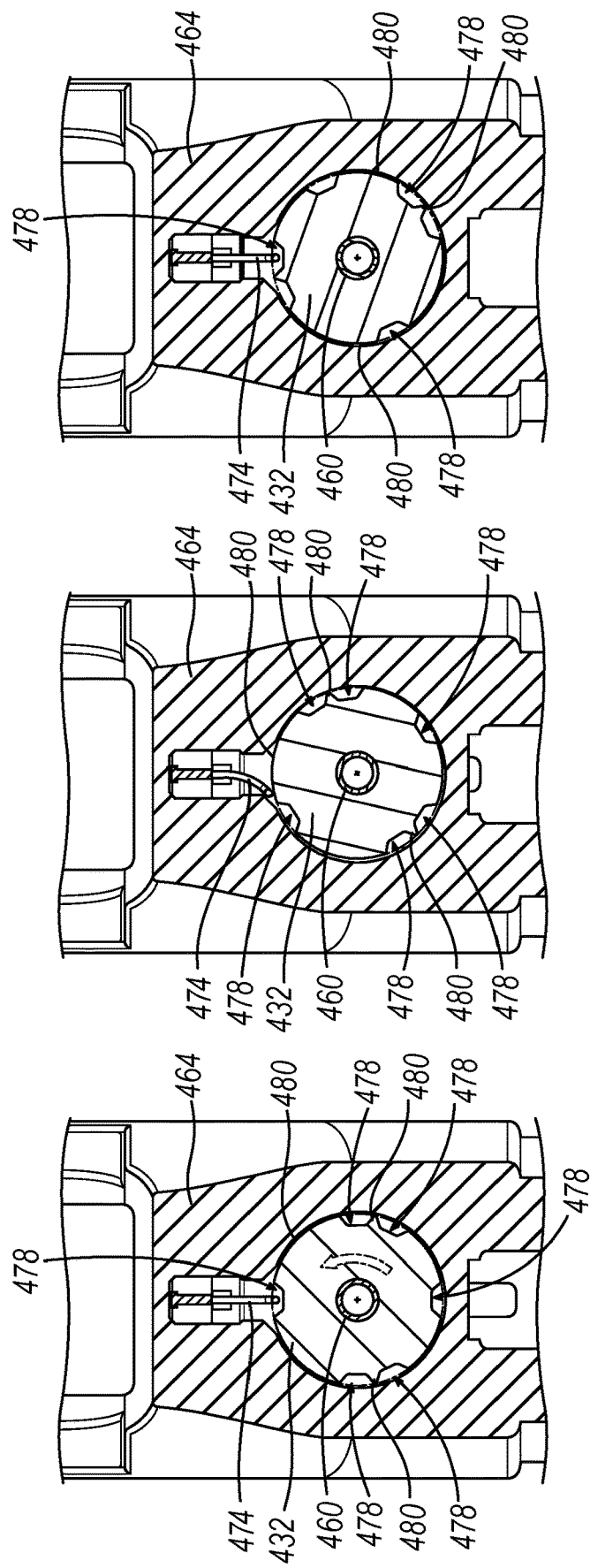

SHAFT DEFLECTION CONTROL ASSEMBLY FOR ENT GUIDE INSTRUMENT

PRIORITY

This application claims priority to U.S. Provisional Pat. App. No. 63/028,609, entitled "Shaft Deflection Control Assembly for ENT Guide Instrument," filed May 22, 2020, the disclosure of which is incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein, in its entirety. An example of such a system is the Relieva® Spin Balloon Sinuplasty System by Acclarent, Inc. of Irvine, California.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Pub. No. 2010/0274188, entitled "Method and System for Treating Target Tissue within the ET," published on Oct. 28, 2010, now abandoned, the disclosure of which is incorporated by reference herein, in its entirety; and U.S. Patent Pub. No. 2013/0274715, entitled "Method and System for Eustachian Tube Dilation," published on Oct. 17, 2013, now abandoned, the disclosure of which is incorporated by reference herein, in its entirety. An example of such a system is the Aera® Eustachian Tube Balloon Dilation System by Acclarent, Inc. of Irvine, California.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein, in its entirety. An example of such an illuminating guidewire is the Relieva Luma Sentry® Sinus Illumination System by Acclarent, Inc. of Irvine, California.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, California. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically. Examples of use of an IGS system in an ENT procedure are described in U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein, in its entirety; and U.S. Pat. No. 10,561,370, entitled "Apparatus to Secure Field Generating Device to Chair," issued Feb. 18, 2020, the disclosure of which is incorporated by reference herein, in its entirety.

It may be desirable to provide easily controlled placement of a balloon of a dilation catheter in an anatomical passageway, including in procedures that will be performed only by a single operator. While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 8A depicts a cross-sectional view of a portion of the instrument of FIG. 2 taken along line 8-8 of FIG. 5, with the deflection control knob and tactile feedback member in a first position;

FIG. 8B depicts a cross-sectional view of a portion of the instrument of FIG. 2 taken along line 8-8 of FIG. 5, with the deflection control knob and tactile feedback member in a second position;

FIG. 8C depicts a cross-sectional view of a portion of the instrument of FIG. 2 taken along line 8-8 of FIG. 5, with the deflection control knob and tactile feedback member in a third position;

Figure 1A:
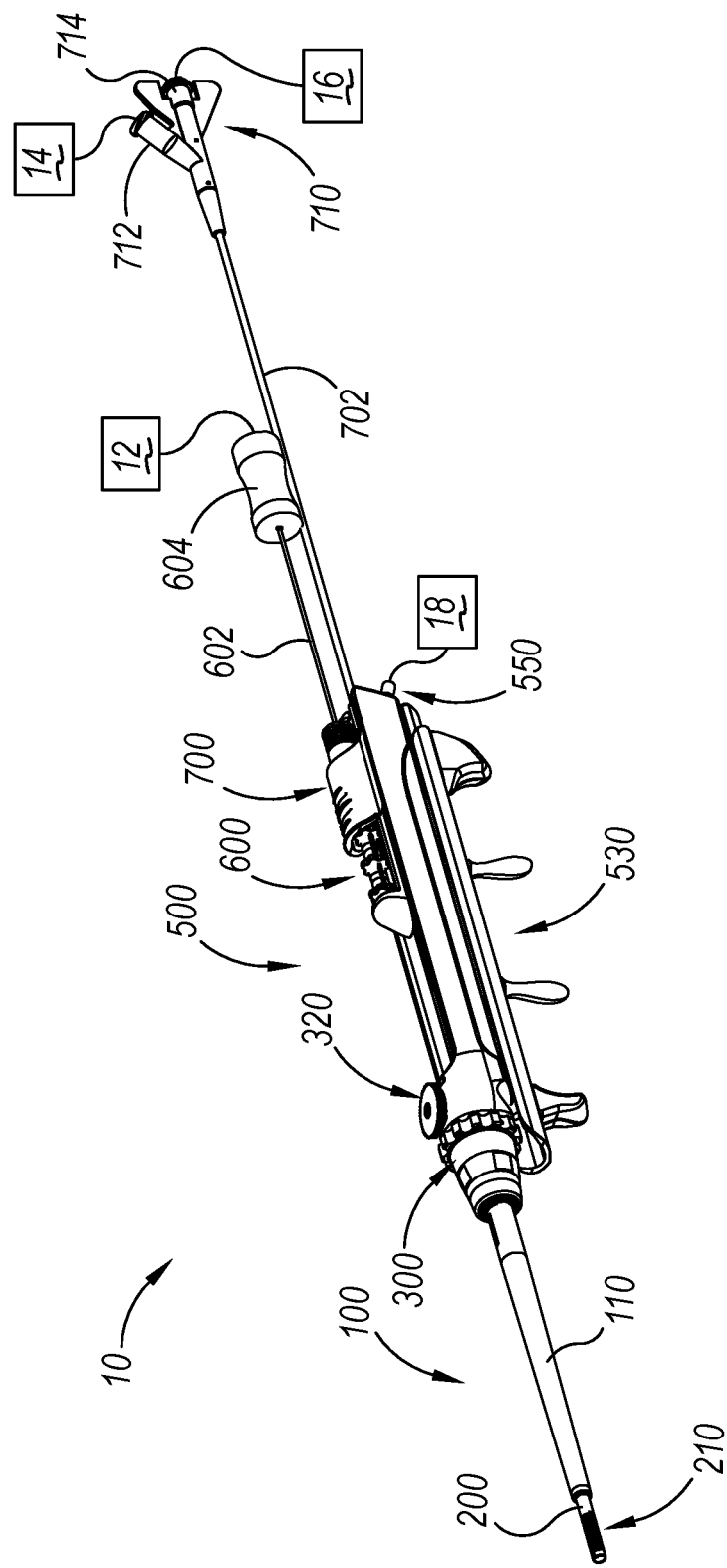
FIG. 1A depicts a perspective view of an exemplary dilation instrument, with a guidewire and a dilation catheter each in respective proximal positions.
Figure 1B:
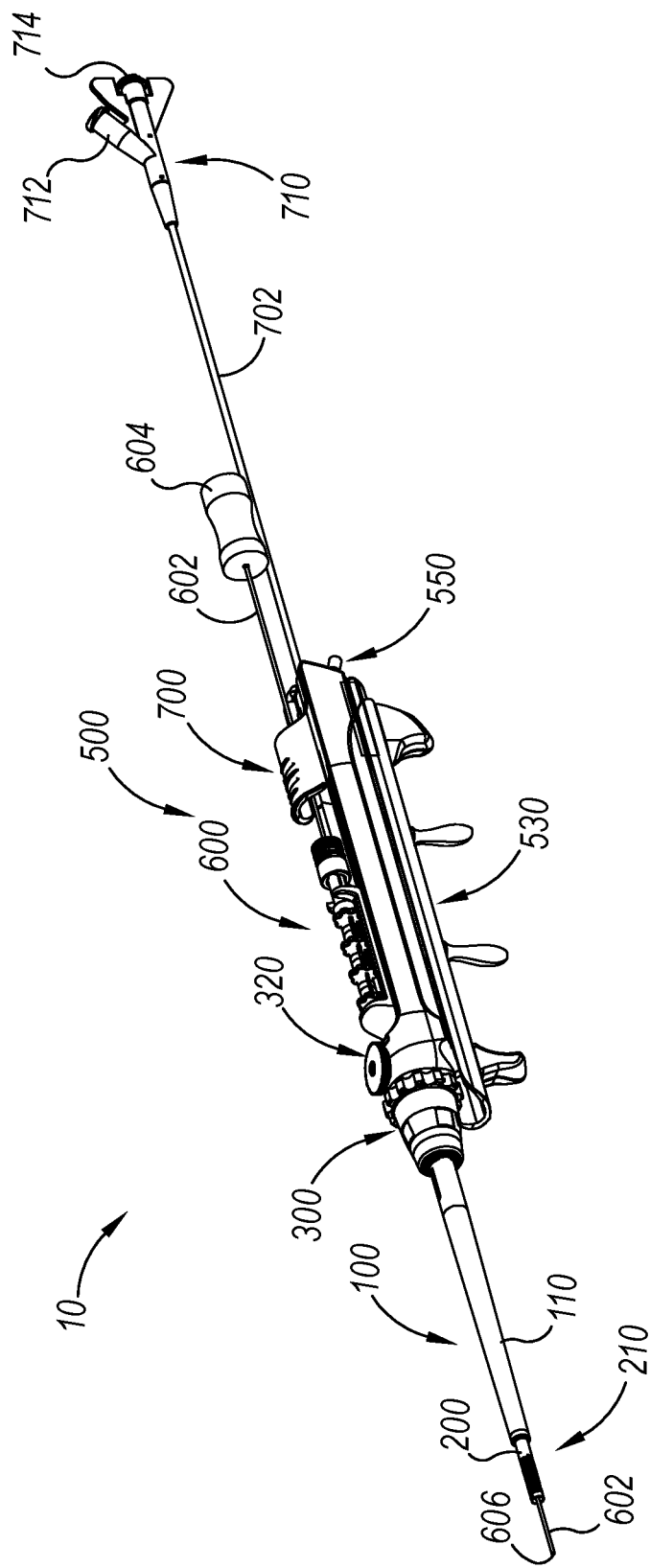
FIG. 1B depicts a perspective view of the instrument of FIG. 1A, with the guidewire in a distal position and the dilation catheter in the proximal position.
Figure 1C:
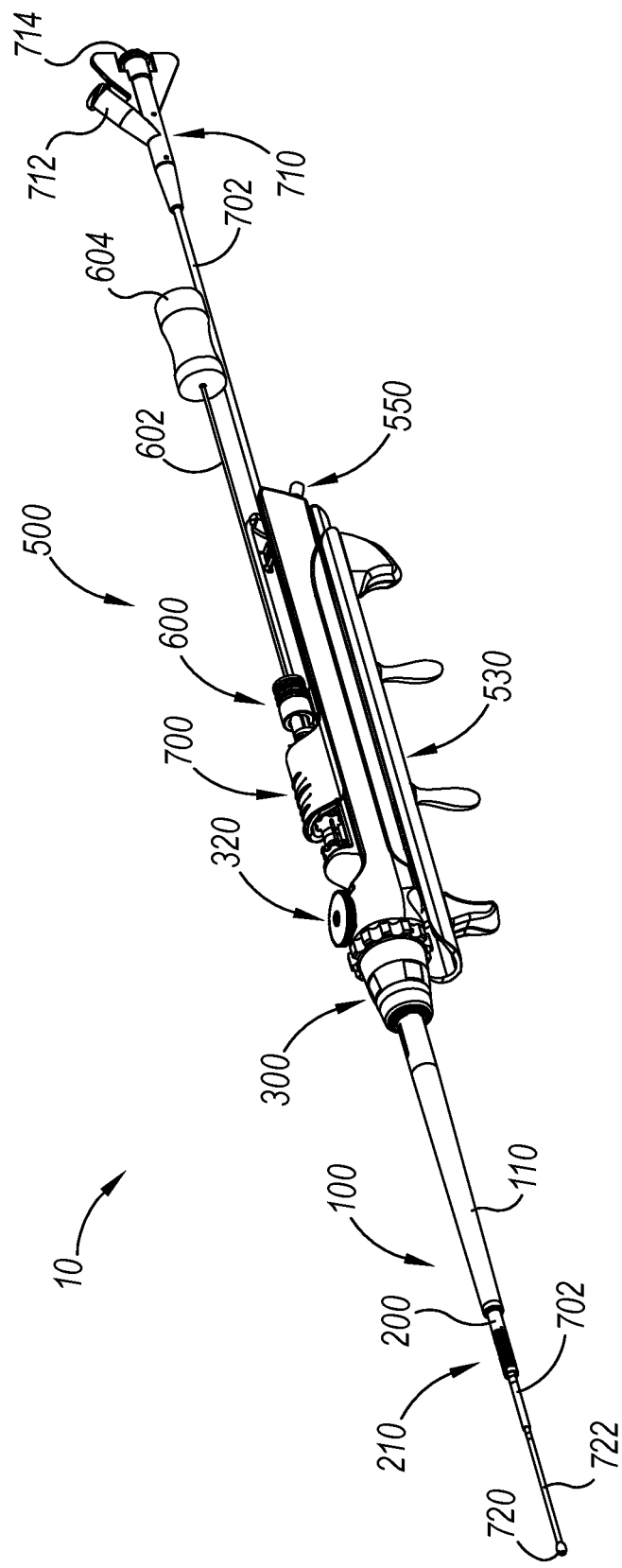
FIG. 1C depicts a perspective view of the instrument of FIG. 1A, with the guidewire and the dilation catheter each in respective distal positions, and with a dilator of the dilation catheter in a non-expanded state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

A. Overview

FIGS. 1A-1D show an exemplary dilation instrument (10) that may be used to dilate the ostium of a paranasal sinus, to dilate another passageway associated with drainage of a paranasal sinus, to dilate a Eustachian tube, or to dilate some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (500), a guide shaft assembly (100) extending distally from handle assembly (500); a guidewire actuation assembly (600) slidably coupled with handle assembly (500); and a dilation catheter actuation assembly (700) slidably coupled with handle assembly (500). A guidewire module (12) is coupled with a guidewire (602) of dilation instrument (10) via a connector (604). An inflation fluid source (14) and an irrigation fluid source (16) are coupled with a dilation catheter (702) of dilation instrument (10) via a connector (710). A suction source (18) is coupled with guide shaft assembly (100) of dilation instrument (10) via a suction port (550) and a conduit (not shown) which spans through handle assembly (500).

Figure 1D:
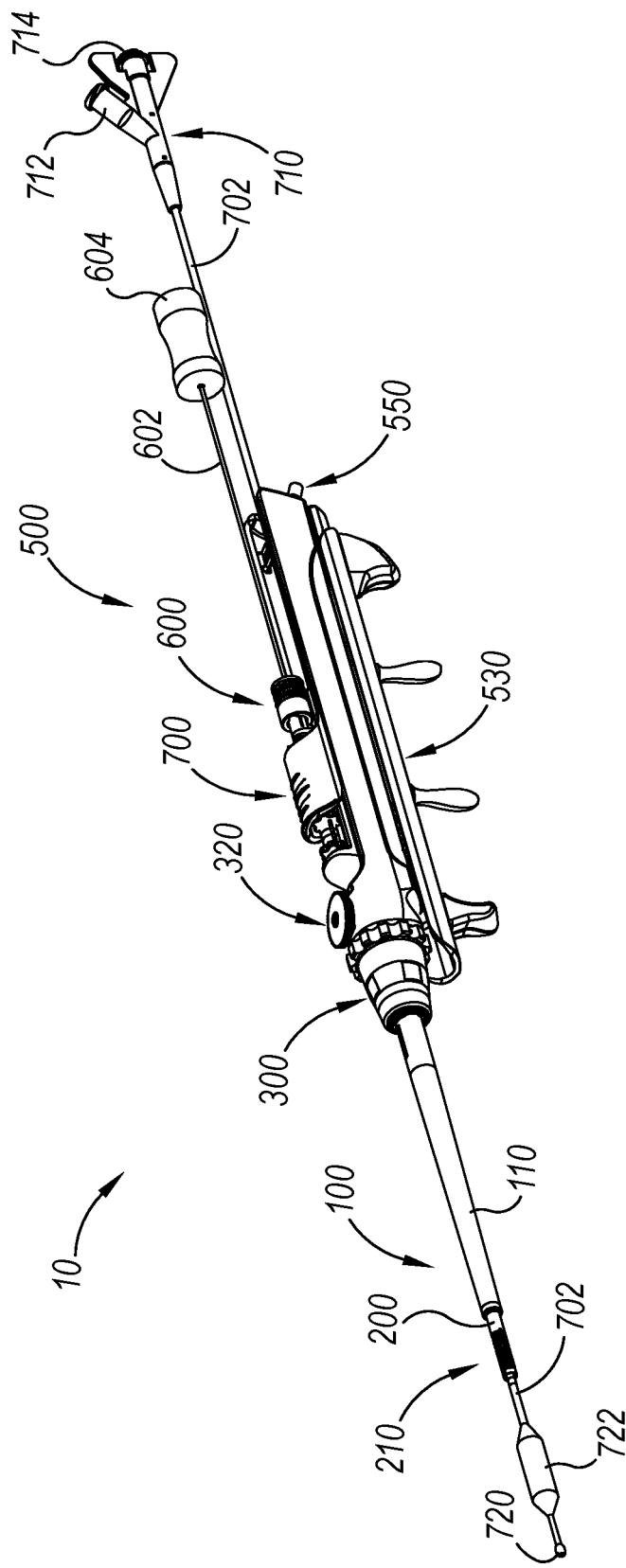
FIG. 1D depicts a perspective view of the instrument of FIG. 1A, with the guidewire and the dilation catheter each in respective distal positions, and with a dilator of the dilation catheter in an expanded state.

Handle assembly (500) is sized and configured to be grasped and operated by a single hand of an operator. The operator may selectively operate guidewire actuation assembly (600) and dilation catheter actuation assembly (700) with the same single hand that grasps handle assembly (500). As shown in the transition from FIG. 1A to FIG. 1B, the operator may advance guidewire actuation assembly (600) distally along handle assembly (500) to thereby advance guidewire (602) distally, such that the distal end (606) of guidewire (602) is positioned distal to the distal end of guide shaft assembly (100). As shown in the transition from FIG. 1B to FIG. 1C, the operator may advance dilation catheter actuation assembly (700) distally along handle assembly (500) to thereby advance dilation catheter (702) distally, such that the distal tip (720) of dilation catheter (702) is positioned distal to the distal end of guide shaft assembly (100). With dilation catheter (702) advanced to a distal position, the operator may then inflate a dilator (722) of dilation catheter (702) to achieve an expanded state as shown in FIG. 1D, to thereby dilate an anatomical passageway in which dilator (722) is positioned.

In the present example, dilation catheter (702) is coaxially disposed within guide shaft assembly (100), and guidewire (602) is coaxially disposed within dilation catheter (702). In some other versions, guide shaft assembly (100) is coaxially disposed within dilation catheter (702), and guidewire (602) is coaxially disposed within guide shaft assembly (100). Also, in some versions, guidewire (602) is omitted.

Figure 2:
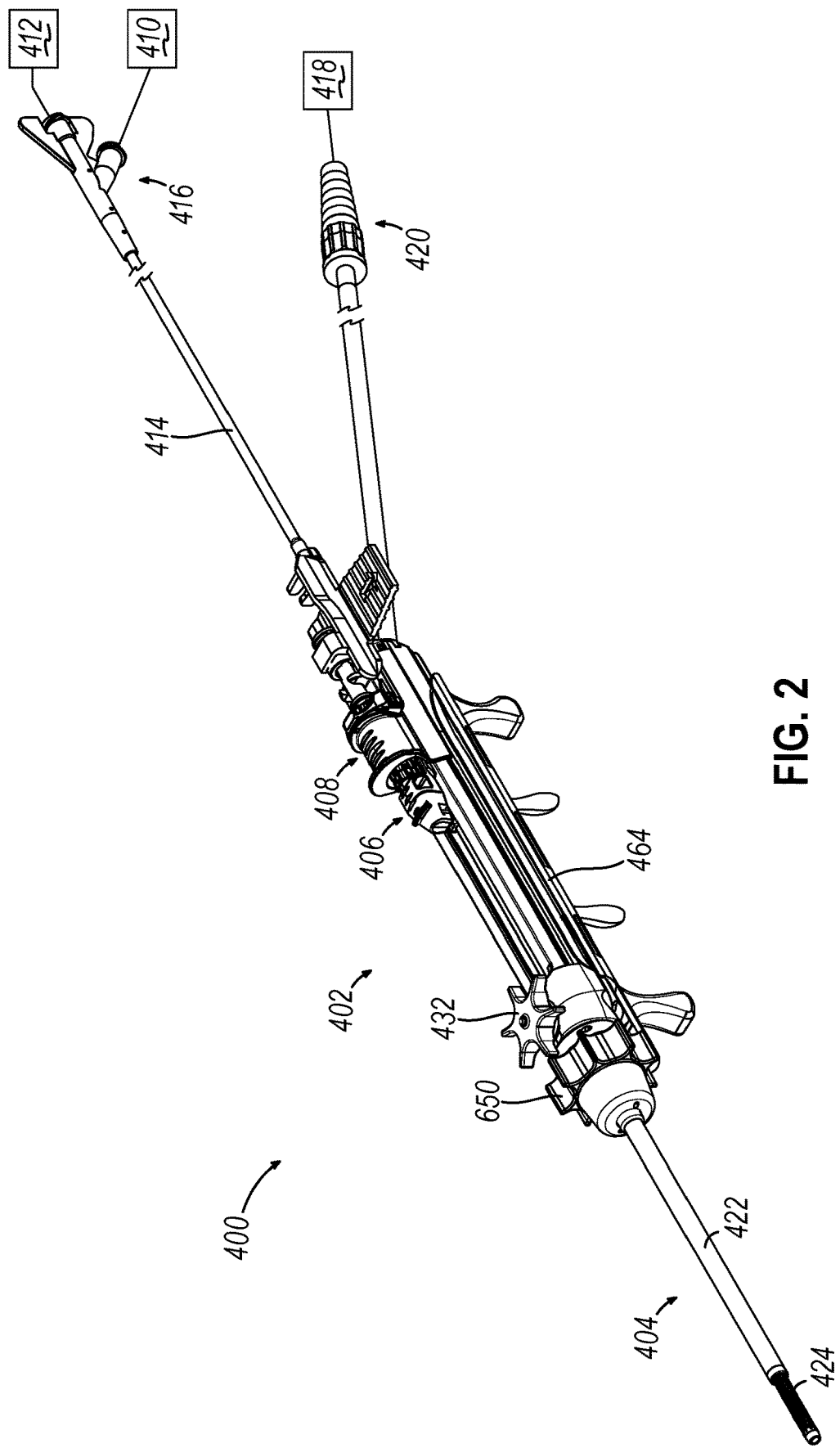
FIG. 2 depicts a perspective view of an exemplary alternative dilation instrument, with a guidewire and a dilation catheter each in respective proximal positions.

FIG. 2 shows an exemplary alternative dilation instrument (400) that may be used to dilate the ostium of a paranasal sinus, to dilate another passageway associated with drainage of a paranasal sinus, to dilate a Eustachian tube, or to dilate some other anatomical passageway (e.g., within the ear, nose, or throat, etc.). Dilation instrument (400) of the present example is operable to provide substantially the same or similar functionality as dilation instrument (10) and is configured and operable just like dilation instrument (10) except for the differences described below. Dilation instrument (400) of this example includes a handle assembly (402), a guide shaft assembly (404) extending distally from handle assembly (402); a guidewire actuation assembly (406) slidably coupled with handle assembly (402); and a dilation catheter actuation assembly (408) slidably coupled with handle assembly (402). A guidewire module (not shown) is coupled with a guidewire (not shown), similar to guidewire module (12) and guidewire (602) of dilation instrument (10). An inflation fluid source (410) and an irrigation fluid source (412) are coupled with a dilation catheter (414) of dilation instrument (400) via a connector (416). A suction source (418) is coupled with guide shaft assembly (404) of dilation instrument (400) via a suction port (420) and a conduit (not shown), which spans through handle assembly (500).

Similar to dilation instrument (10), the operator may advance guidewire actuation assembly (406) distally along handle assembly (402) to thereby advance a guidewire distally. The operator may also advance dilation catheter actuation assembly (408) distally along handle assembly (402) to thereby advance dilation catheter (414) distally, such that the distal tip (not shown) of dilation catheter (414) is positioned distal to the distal end of guide shaft assembly (404). With dilation catheter (414) advanced to a distal position, the operator may then inflate a dilator, such as one similar to dilator (722) of instrument (10), to achieve an expanded state as shown in FIG. 1D, to thereby dilate an anatomical passageway in which dilator (722) is positioned.

In the present example, dilation catheter (414) is coaxially disposed within guide shaft assembly (404), and a guidewire is coaxially disposed within dilation catheter (414). In some other versions, guide shaft assembly (404) is coaxially disposed within dilation catheter (414), and a guidewire is coaxially disposed within guide shaft assembly (404). Also, in some versions, as shown in FIG. 2, the guidewire is omitted.

Examples of features and functionalities of the above-noted components of dilation instrument (400) are described in greater detail below. These features and functionalities are merely illustrative examples. By way of further example only, the features and functionalities described herein may be modified in accordance with the teachings of U.S. Pat. No. 10,874,839, entitled "Adjustable Instrument for Dilation of Anatomical Passageway," issued Dec. 29, 2020, and U.S. Pat. Pub. No. 2019/0015646, entitled "Adjustable Instrument for Dilation of Anatomical Passageway," published Jan. 17, 2019, issued as U.S. Pat. No. 11,027,105 on Jun. 8, 2021, the disclosures of which are incorporated by reference herein, in their entirety. Other variations of the features and functionalities described herein will be apparent to those skilled in the art in view of the teachings herein.

B. Exemplary Guide Shaft Assembly and Deflection Actuation Assemblies

FIGS. 3-12B show various components of guide shaft assembly (404) in greater detail. Guide shaft assembly (404) of this example includes a rigid shaft member (422), a flexible shaft member (424), a push-pull wire (426), a cam barrel (428), a translatable member such as pull sleeve (430), and rotary actuators, such as deflection control knob (432) and shaft rotation assembly (498). Shaft members (422, 424), cam barrel (428), pull sleeve (430), and deflection control knob (432) are coaxially aligned with each other in this example, with push-pull wire (426) being laterally offset from the longitudinal axis (434) shared by shaft members (422, 424), cam barrel (428), pull sleeve (430), and deflection control knob (432). As will be described in greater detail below, guide shaft assembly (404) is operable to guide a guidewire, similar to guidewire (602) of dilation instrument (10), and dilation catheter (414) along an operator-selected exit angle relative to the central longitudinal axis (434) of guide shaft assembly (404).

In some versions, both shaft members (422, 424) are formed of a metallic material, such as stainless steel and/or nitinol. In some such versions, shaft members (422, 424) (and at least some other portions of instrument (400)) may be reusable, with such reusable components being subject to cleaning and sterilization between uses on different patients. In some other versions, one or both of shaft members (422, 424) may be formed of a polymeric material. In some such versions, shaft members (422, 424) may be treated as single-use-only components. Flexible shaft member (424) is secured to rigid shaft member (422) and is positioned distally in relation to rigid shaft member (422).

Figure 4A:
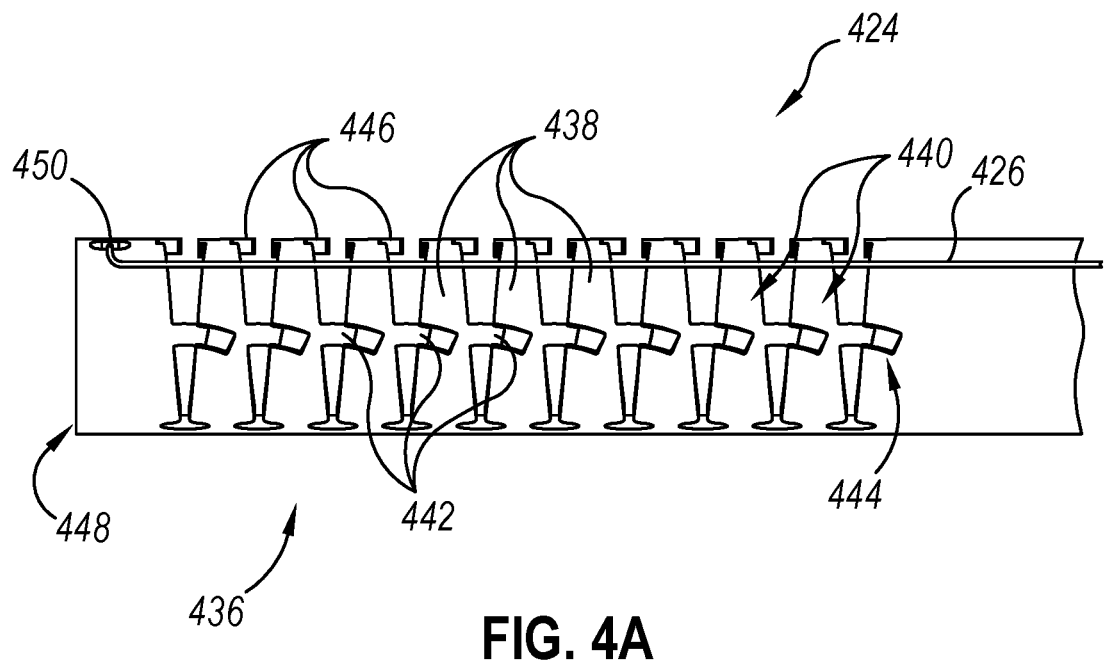
FIG. 4A depicts a side view of the flex section of the instrument of FIG. 2, with the flex section in a non-deflected state.
Figure 4B:
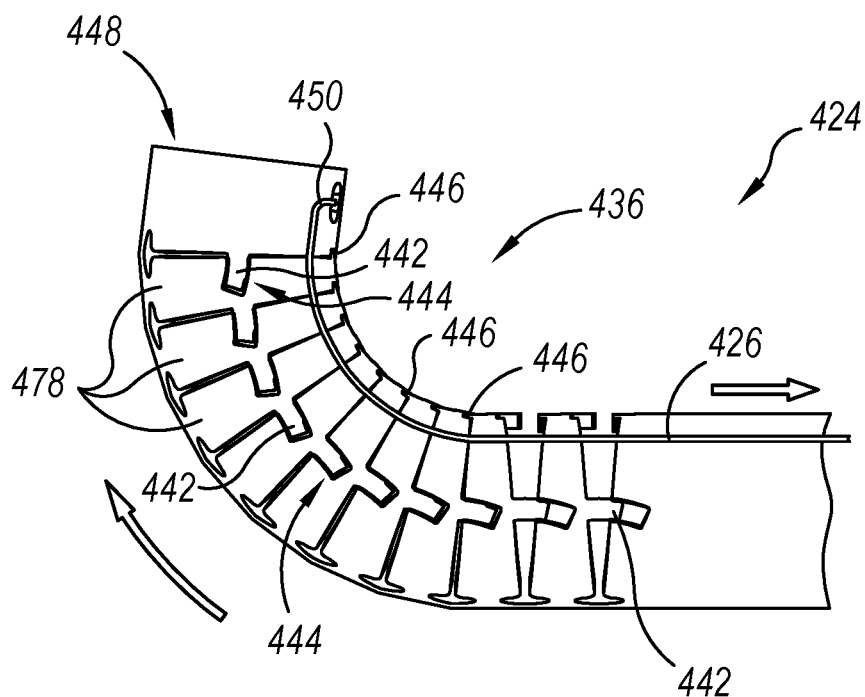
FIG. 4B depicts a side view of the flex section of the instrument of FIG. 2, with the flex section in a deflected state.

As best seen in FIGS. 4A-4B, flexible shaft member (424) includes a flex section (436) that is formed by a series of ribs (438), which are separated by a series of notches (440). Notches (440) are generally V-shaped, with a circular opening at the vertex of each "V." Notches (440) also include tab portions (442) that fit in corresponding sub-notches (444). The top of each "V" includes a set of stop features (446). As shown in FIG. 4A, when flex section (436) is in a straight configuration, tab portions (442) are disposed in corresponding sub-notches (444) but are not fully seated in sub-notches (444). As also shown in FIG. 4A, when flex section (436) is in a straight configuration, stop features (446) are separated from each other. FIG. 4B shows flex section (436) in a fully bent configuration. In this state, tab portions (442) are fully seated in sub-notches (444) and stop features (446) are engaged with each other. During the transition between the states shown in FIGS. 4A-4B, tab portions (442) and sub-notches (444) may cooperate to ensure that flex section (436) bends in a consistent fashion, with sufficient lateral stability; and that flex section (436) provides a consistent and stable bent or straight state.

By way of example only, flex section (436) may be formed through laser cutting or any other suitable manufacturing process. In some versions, flex section (436) is covered with a flexible wrap (not shown). Such a flexible wrap may prevent tissue and other structures from getting snagged or pinched in notches (440), without compromising the flexibility of flex section (436). A flexible wrap may also ensure that suction provided through guide shaft assembly (404) is focused at distal end (448). Various suitable forms that flex section (436) may take will be apparent to those of ordinary skill in the art in view of the teachings herein. By way of further example only, flex section (436) may be constructed and operable in accordance with at least some of the teachings of U.S. Pat. Pub. No. 2018/0311472, entitled "Deflectable Guide for Medical Instrument," published Nov. 1, 2018, issued as U.S. Pat. No. 11,376,401 on Jul. 5, 2022, the disclosure of which is incorporated by reference herein, in its entirety.

Figure 3:
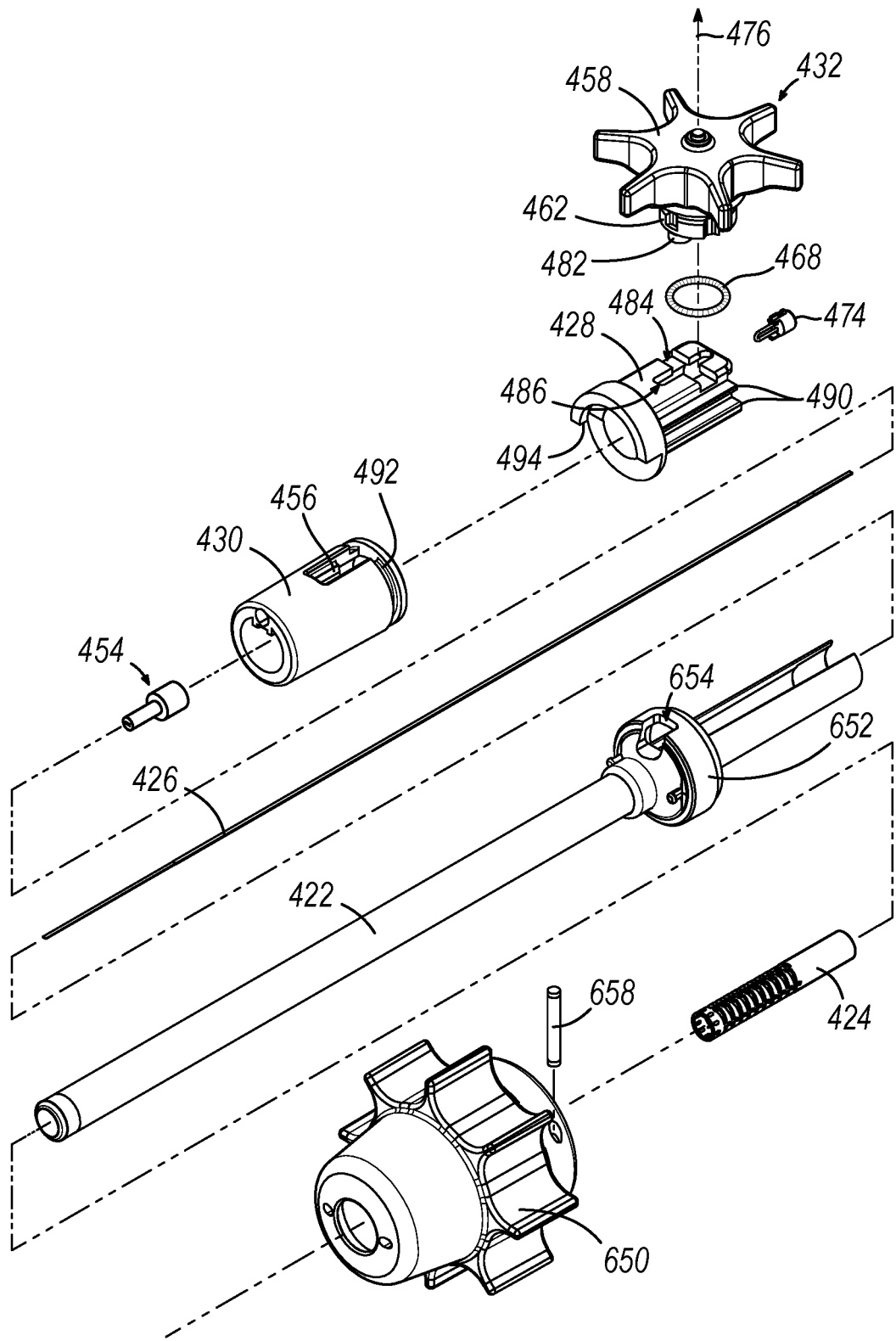
FIG. 3 depicts an exploded perspective view of a guide shaft assembly of the instrument of FIG. 2.
Figure 5:
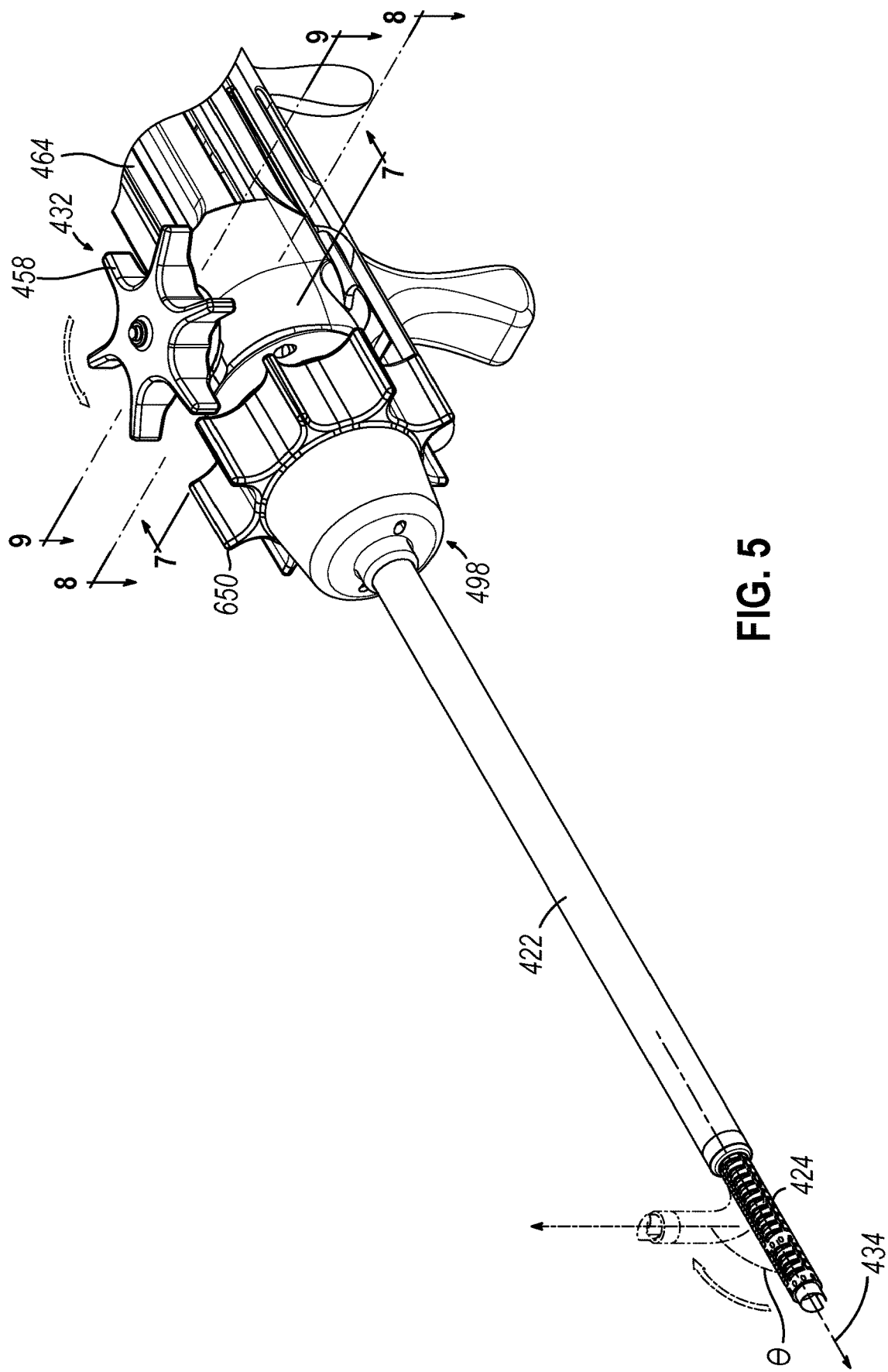
FIG. 5 depicts a perspective view of a guide shaft assembly of the instrument of FIG. 2, with the deflection control knob being rotated and the flex section deflecting away from the longitudinal axis of the guide shaft assembly.
Figure 11A:
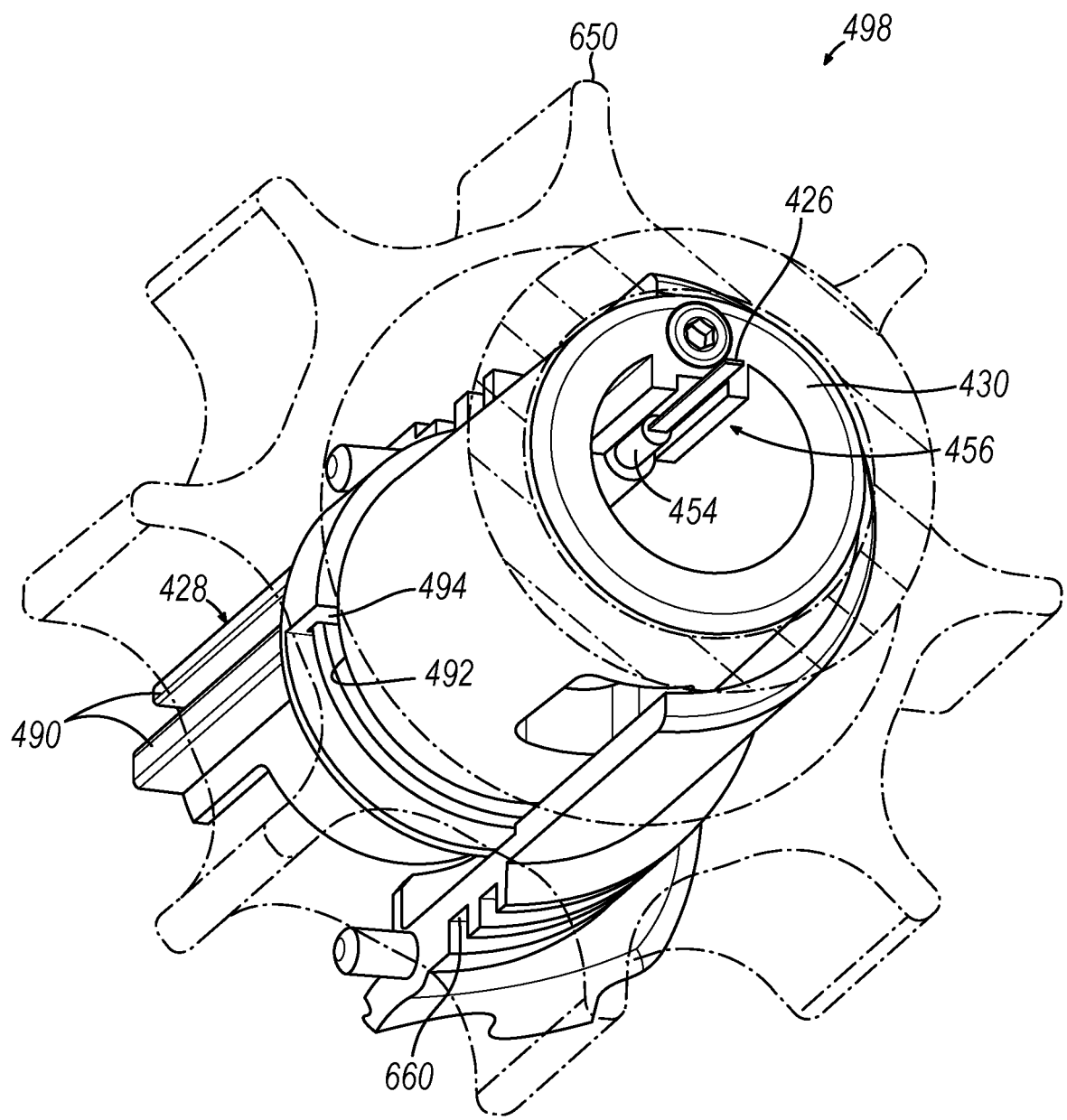
FIG. 11A depicts a perspective view of a portion of the instrument of FIG. 2, with a housing portion removed from a handle assembly of the instrument to reveal internal components at the distal end of the handle assembly, with the shaft rotation control knob shown as transparent and rotated to a first position.
Figure 11B:
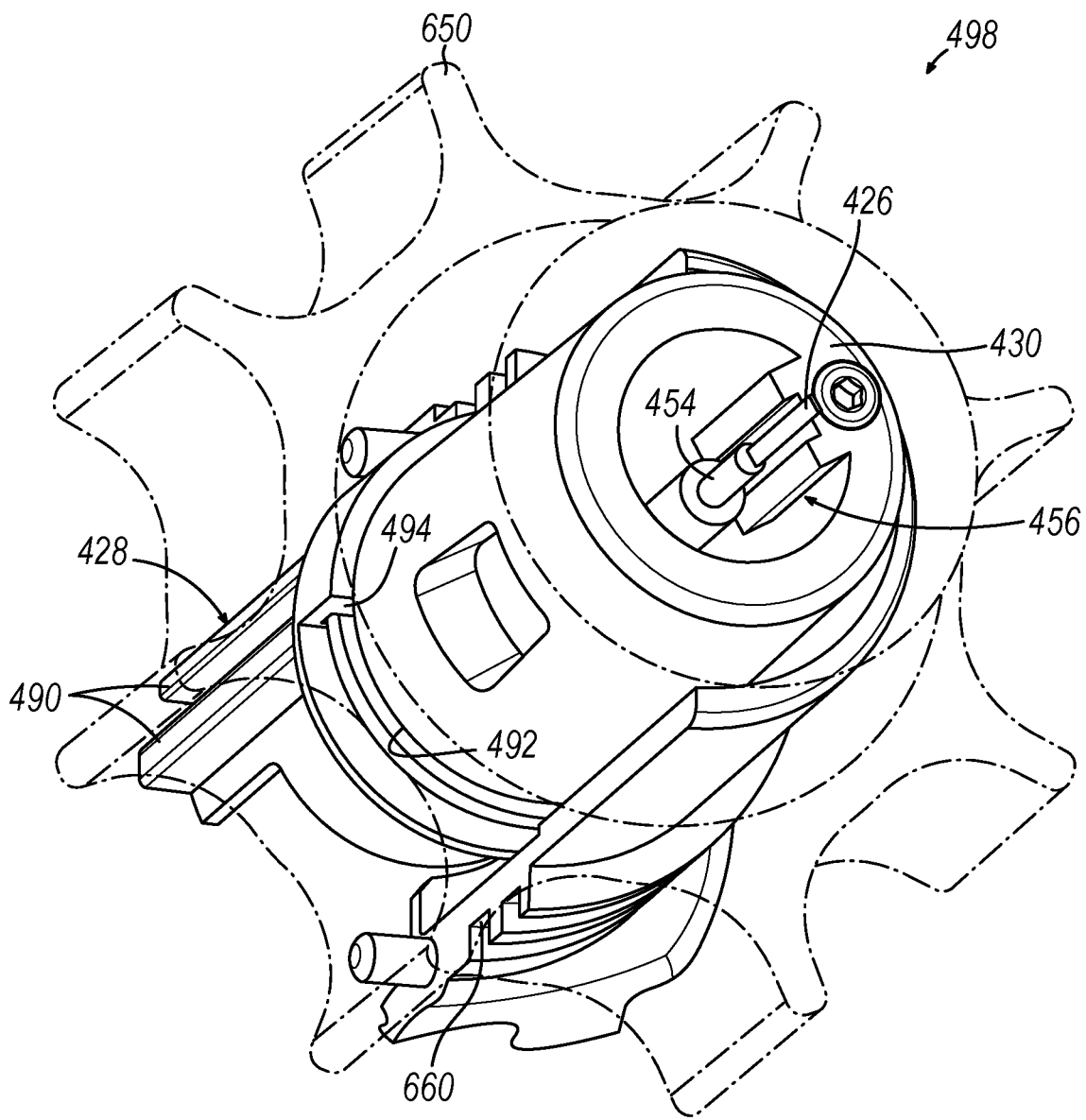
FIG. 11B depicts a perspective view of a portion of the instrument of FIG. 2, with a housing portion removed from a handle assembly of the instrument to reveal internal components at the distal end of the handle assembly, with the shaft rotation control knob shown as transparent and rotated to a second position.

Push-pull wire (426) is disposed within shaft members (422, 424) and is operable to provide controlled bending of flex section (436). As shown in FIGS. 4A-4B, a distal end (450) of push-pull wire (426) is secured to the distal end (448) of flexible shaft member (424), distal to flex section (436). Push-pull wire (426) is disposed near the tops of the "V"s of notches (440). Thus, when push-pull wire (426) is pulled proximally, flex section (436) will bend to a deflected configuration. When push-pull wire (426) is pushed distally, flex section (436) will bend toward a straight configuration. A proximal end (452) of push-pull wire (426) couples with a retention holder (454) (FIG. 3 and FIGS. 11A-11B) which is secured to pull sleeve (430) by a retention key (456) (FIG. 3 and FIGS. 11A-11B). More specifically, proximal end (452) is coupled with retention holder (454); and retention holder (454) is inserted into retention key (456), which is formed as an inner cavity within pull sleeve (430) having a complementary size and shape to mate with retention holder (454) such that longitudinal movement along axis 434) of pull sleeve (430) results in complementary longitudinal movement along axis (434) of push-pull wire (426). As is illustrated in FIG. 5 and will be described in greater detail below, rotation of the deflection control knob (432) causes longitudinal translation of push-pull wire (426), and longitudinal translation of push-pull wire (426) thereby causes straightening or bending of flex section (436).

Figure 6:
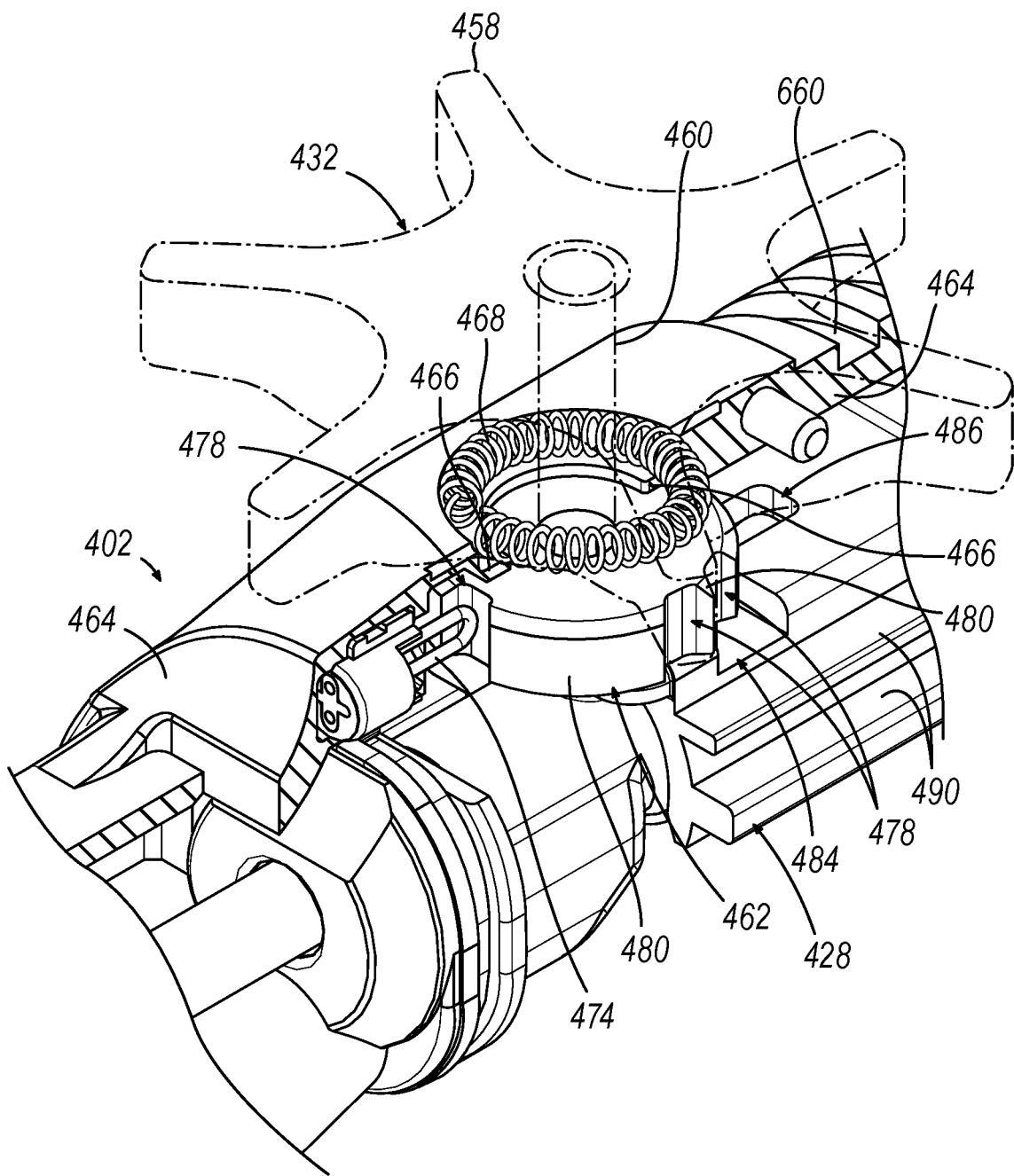
FIG. 6 depicts a perspective view of a portion of the instrument of FIG. 2, with a housing portion removed from a handle assembly of the instrument to reveal internal components at the distal end of the handle assembly.
Figure 7:
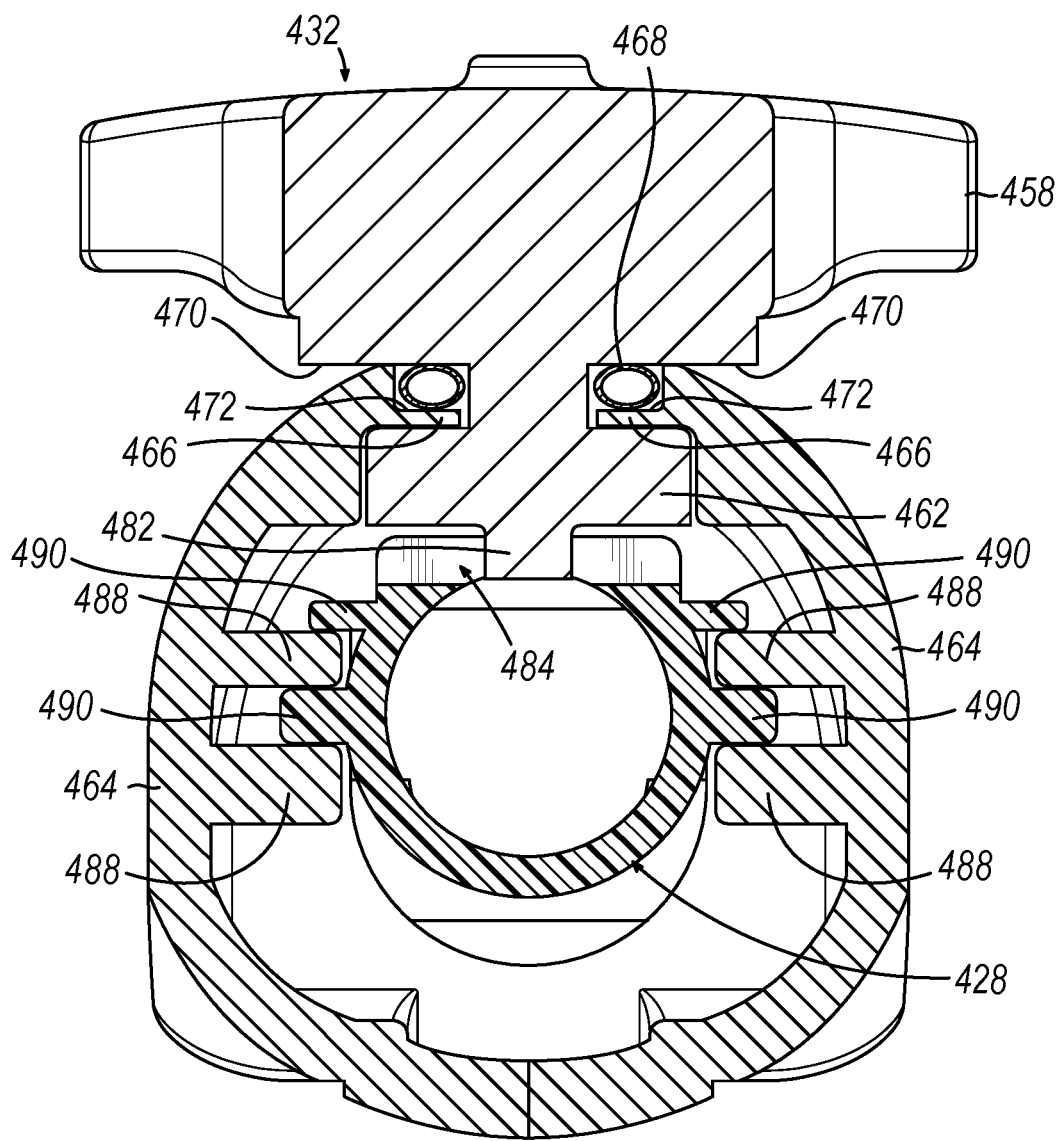
FIG. 7 depicts a cross-sectional view of a portion of the instrument of FIG. 2 taken along line 7-7 of FIG. 5.

As shown in FIG. 3 and FIGS. 6-7, deflection control knob (432) includes a thumbwheel (458), a shaft (460), and a notched gear (462). As shown in FIGS. 6-7, deflection control knob (432) is secured to the housing (464) of handle assembly (402) such that thumbwheel (458) is above the housing (464), with shaft (460) being captured between housing (464). Thumbwheel (458) is positioned such that an operator may rotate thumbwheel (458) relative to housing (464) using the thumb of the hand that is grasping handle assembly (402). A resilient member, such as spring (468), is positioned along the exterior of shaft (460) to engage housing (464). Specifically, spring (468) is positioned between lower surface (470) of thumbwheel (458) and upper surface (472) of flanges (466) of housing (464). In some versions, spring (468) is a compression spring formed into a toroidal shape. In alternative versions, the ends of spring (468) or conjoined in the toroidal shape to form a garter spring. Spring (468) is positioned between lower surface (470) of thumbwheel (458) and upper surface (472) of flanges (466) of housing (464) such that spring (468) is radially compressed forming an elliptical shape. As such, spring (468) applies a constant frictional force of resistance against rotational movement of the deflection control knob (432) relative to housing (464). As result, spring (468) increases the minimum force required for the operator to rotate deflection control knob (432) and deflection control knob (432) is therefore less susceptible to permitting unintentional or otherwise unwanted rotational movements which may cause errors during operation of dilation instrument (400). Further, while spring (468) increases the force required to rotate deflection control knob (432), spring (468) does not restrict the rotational degree of which deflection control knob (432) may be rotated. As such, deflection control knob (432) is infinitely rotatable about any number of rotational positions, as desired.

As will be described in greater detail below, flex section (436) of flexible shaft member (424) is configured to deflect away from the longitudinal axis (434) of guide shaft assembly (404) when deflection control knob (432) is rotated about an axis (476) perpendicular to the longitudinal axis (434) of guide shaft assembly (404). As deflection control knob (432) is rotated, notched gear (462) of deflection control knob (432) is positioned to engage a feedback member (474) which is configured to provide a tactile and audible feedback to the operator. This feature may optionally be included in dilation instruments (400) used in some operations, such as those conducted in dim lighting to allow better viewing of an image guidance monitor or better viewing of an illuminating guidewire. Requiring the operator to shift her eyes from a monitor to dilation instrument (400) to verify rotational positioning of deflection control knob (432) may cause problems such as loss of endoscope position, mispositioning of a balloon sinuplasty device, or other problems. As such, feedback member (474) can be included to provide the operator with a tactile feedback, such as an audible noise or a vibration, indicating the rotational position of deflection control knob (432). Feedback member (474) may include any material operable to flex and provide sound or vibrational feedback upon being released from the flexed position. For example, feedback member (474) may include materials such as polyester, nylon, polyetheretherketone film, a stainless steel spring, a looped stainless steel wire, a nitinol wire, a spring-applied linear plunger, a hard-plastic strip, and/or any devices of other suitable materials.

As shown in FIGS. 8A-8C, feedback member (474) may be coupled with housing (464) and positioned adjacent notched gear (462) of deflection control knob (432). Feedback member (474) may be configured to cooperate with a feedback portion of the notched gear (462) as the deflection control knob (432) is rotated, wherein the cooperation is operable to produce a tactile and audible feedback indication to a user. Feedback portion of notched gear (462) is defined by one or more detent portions (478) separated by one or more protruding portions (480). In a first position, shown in FIG. 8A, feedback member (474) may extend into a detent portion (478). Shown in FIG. 8B, as deflection control knob (432) (and therefore notched gear (462)) is rotated, feedback member (474) is configured to bend as it contacts protruding portion (480). Shown in FIG. 8C, feedback member (474) moves or "snaps" back to a straightened configuration once it reaches detent portions (478). As feedback member (474) moves back into a straightened configuration, an audible noise, such as a click, or a vibration occurs to indicate to the operator that a desired rotational position of the deflection control knob (432) has been reached, and therefore a desired deflection angle (Θ) (see FIG. 5) of flex section (436) has been achieved. As such, detent portions (478) may be predefined on notched gear (462) to correspond to one or more desired degrees of deflection of the flex section (436) away from the longitudinal axis (434). For example, notched gear (462) can include detents which promote three tactile feedbacks to the operator. These three example detent portions (478) may be configured to correspond to 55-degree, 70-degree, and 110-degree deflection angles (Θ) of the flex section (436) relative to the longitudinal axis (434). These three example angles (Θ) may be configured specifically to allow guide shaft assembly (404) to be inserted into any one of three or more distinct paranasal sinus ostia or other passageways (e.g., Eustachian tube, etc.).

Once the operator achieves a desired angle of deflection of flex section (436), detent portions (478) may provide self-locking functionality such that flex section (436) may maintain the selected angle of deflection during subsequent normal use of instrument (400), until the operator again rotates deflection control knob (432) relative to rigid shaft member (422) to further adjust the angle of deflection. Since a guidewire and dilation catheter (414) may be slidably positioned within guide shaft assembly (404), the guidewire and dilation catheter (414) will exit the distal end of guide shaft assembly (404) at whatever deflection angle the operator has selected. In view of the foregoing, an operator may readily achieve various exit angles for the guidewire and dilation catheter (414) by rotating deflection control knob (432) relative to rigid shaft member (422). The operator may thus readily dilate various anatomical passageways without having to exchange instruments; and without having to replace pieces of instrument (400).

Figure 9A:
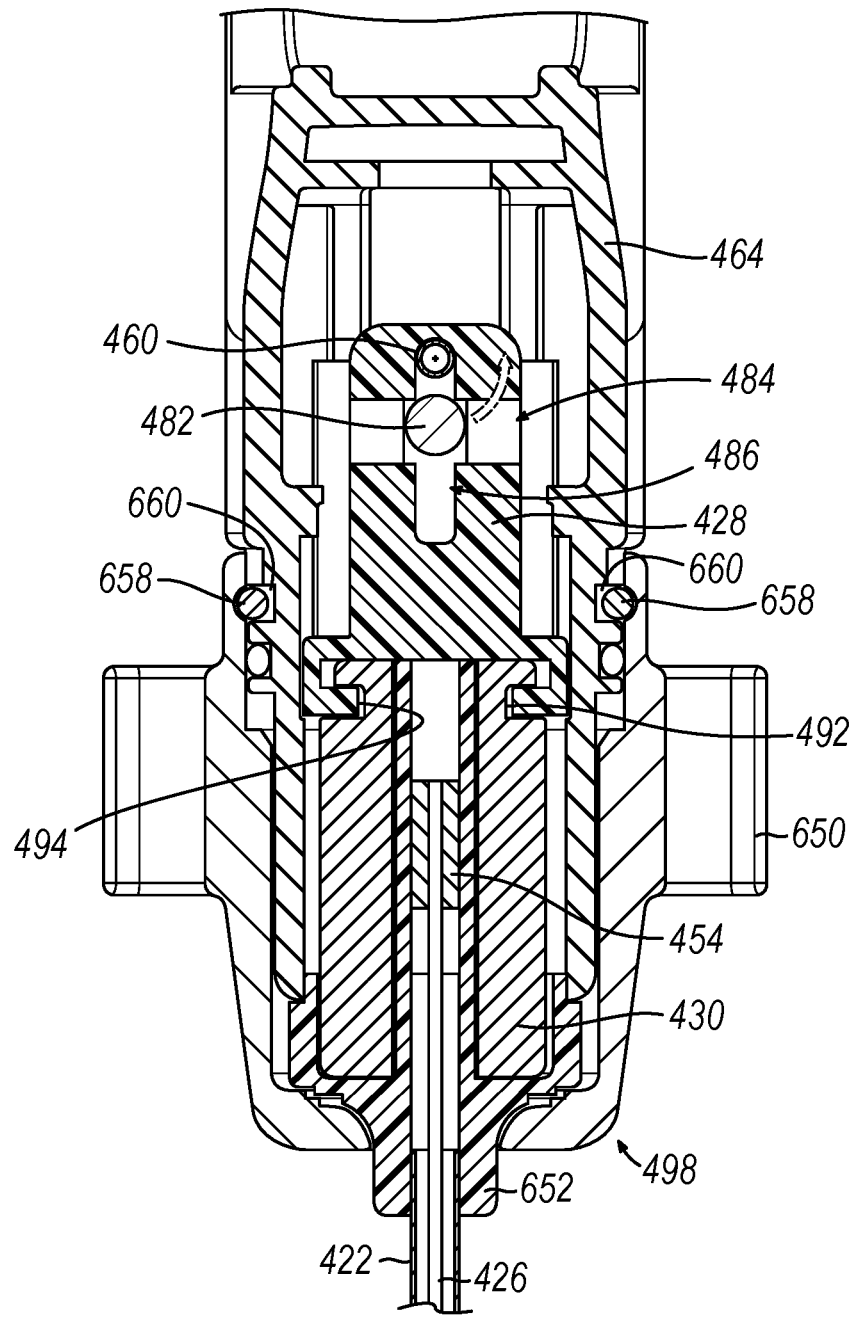
FIG. 9A depicts a cross-sectional view of a portion of the instrument of FIG. 2 taken along line 9-9 of FIG. 5, with the deflection control knob and cam barrel in a first position.
Figure 9B:
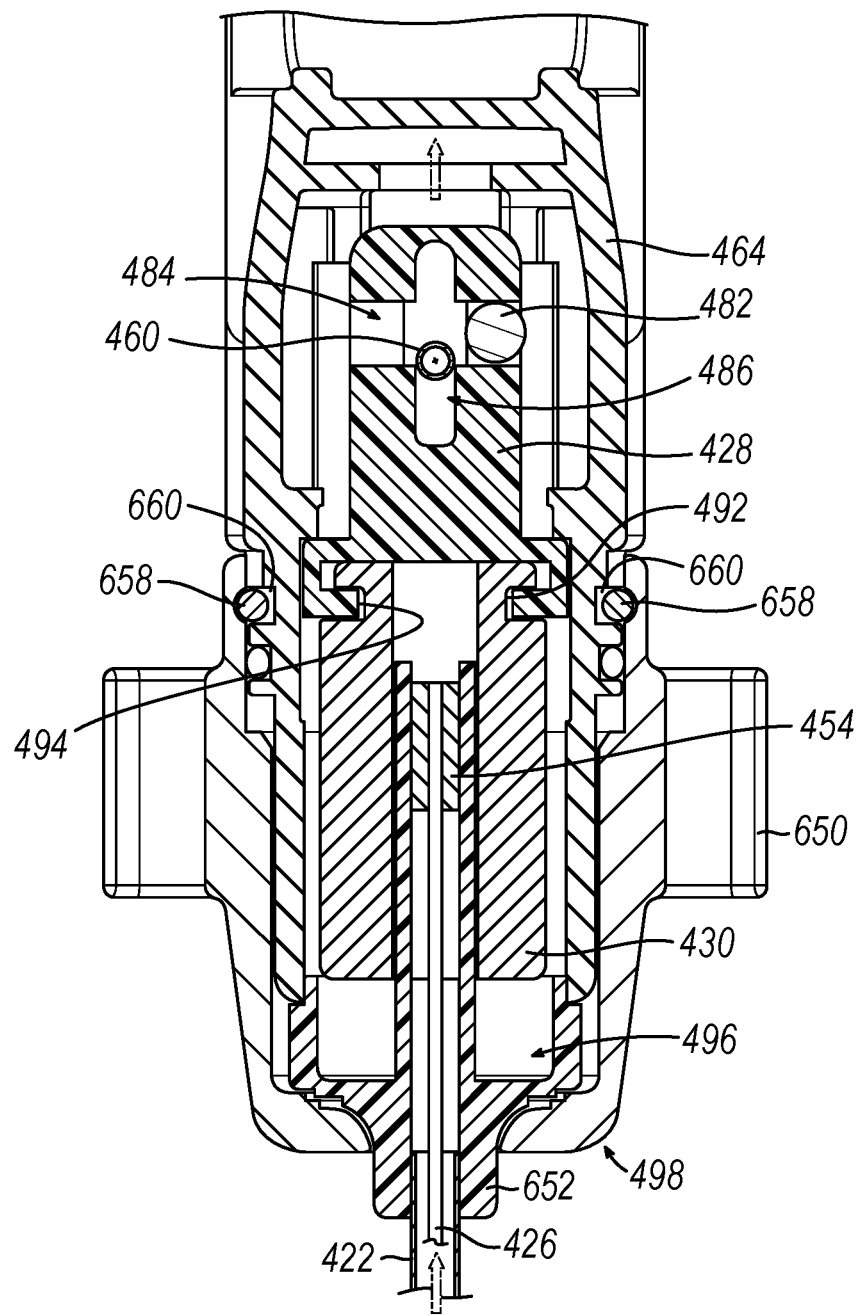
FIG. 9B depicts a cross-sectional view of a portion of the instrument of FIG. 2 taken along line 9-9 of FIG. 5, with the deflection control knob and cam barrel a second position.

As shown in FIGS. 9A-9B, deflection of flex section (436) of guide shaft assembly (404) is operable using push-pull wire (426), cam barrel (428), pull sleeve (430), and deflection control knob (432). Further, deflection control knob (432) includes a pin (482) to translate cam barrel (428) longitudinally (distally and proximally) along longitudinal axis (434). Pin (482) is sized and shaped to insert into a cam slot (484), which may in some versions include a linear recess spanning perpendicular to the longitudinal axis (434) that is formed into a top surface of cam barrel (428). Pin (482) is laterally offset relative to shaft (460) and the axis of rotation of deflection control knob (432). As shown in FIG. 7 and FIG. 9A, pin (482) is positioned centrally within cam slot (484) and is operable to rotate along an orbital path, about the axis of rotation of deflection control knob (432), as deflection control knob (432) is rotated by a user. As pin (482) traverses this orbital path, the motion of pin (482) has both a longitudinal directional component and a transverse directional component. As such, the directional component transverse to the longitudinal axis (434) transitions pin (482) through cam slot (484), while the longitudinal directional component pushes and pulls cam barrel (428) distally and proximally. As shown in FIG. 9B, deflection control knob (434), and therefore pin (482), are shown rotated in a one-quarter turn in a counterclockwise direction, resulting in cam barrel (428) translating proximally relative to housing (464) of handle assembly (402). As deflection control knob (434) is rotated another one-quarter turn, cam barrel (428) is pulled proximally as far as it is capable of being pulled. After another one-quarter turn, cam barrel (428) is translated distally back to a similar position as is shown in FIG. 9B. Finally, after the fourth one-quarter turn, cam barrel (428) returns to its far-most distal position, as shown in FIG. 9A.

Cam barrel (428) includes additional features to permit longitudinal translation relative to housing (464) of handle assembly (402). For example, cam barrel (428) includes a longitudinal recess (486) sized and shaped to permit shaft (460) of deflection control knob (432) to pass through during longitudinal translation. Further, as shown in FIG. 7, cam barrel (428) is coupled with rigid rails (488) formed by the inner region of housing (464), such that cam barrel (428) is allowed to slide longitudinally along rails (488); yet cam barrel (428) is prevented from shifting or rotating about longitudinal axis (434). As shown in FIG. 7, one or more tabs (490) project laterally and unitarily from cam barrel (428) and are configured to mate with rails (488). As such, cam barrel (428) is slidably disposed within and relative to housing (464) of handle assembly (402). Other suitable structures may be used to achieve this relationship between rails (488) and cam barrel (428).

As noted above, proximal end (452) of push-pull wire (426) is secured to pull sleeve (430), such that push-pull wire (426) translates with pull sleeve (430) relative to rigid shaft member (422) in response to rotation of deflection control knob (432) relative to rigid shaft member (422). As shown in FIGS. 9A-9B, one side of the proximal portion of pull sleeve (430) includes a slot (492). Slot (492) is configured to mate with a rib (494) of cam barrel (428). As such, with push-pull wire (426) coupled with pull sleeve (430), and pull sleeve (430) effectively secured to cam barrel (428), pull sleeve (430) and push-pull wire (426) translate distally and proximally relative to rigid shaft member (422) as deflection control knob (432) is rotated. As can be seen in FIG. 9B, translating the push-pull wire (426), pull sleeve (430), and cam barrel (428) in a proximal direction results in an air gap (496) being formed between pull sleeve (430) and shaft rotation assembly (498). As also noted above, translation of push-pull wire (426) relative to rigid shaft member (422) causes lateral deflection of flex section (436). The operator may thus selectively deflect flex section (436) by rotating deflection control knob (432) relative to rigid shaft member (422).

C. Exemplary Shaft Rotation Assembly

Figure 10:
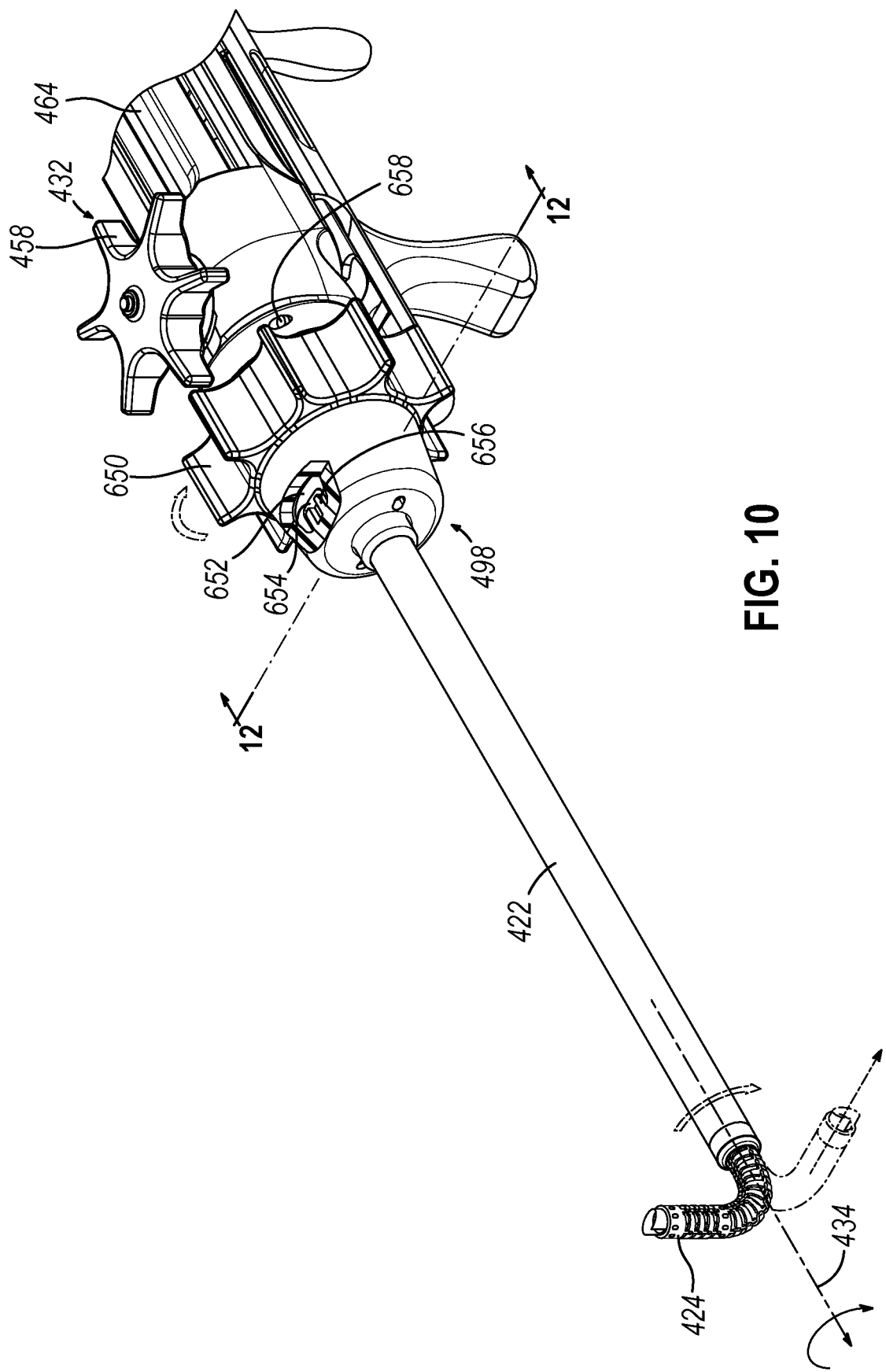
FIG. 10 depicts a perspective view of a guide shaft assembly of the instrument of FIG. 2, with the shaft rotation control knob being rotated and the flex section rotating about the longitudinal axis of the guide shaft assembly.

In addition to providing control for the deflection of flex section (436) to facilitate access to various anatomical passageways, it may be desirable to enable rotation of guide shaft assembly (404) about the longitudinal axis (434) of guide shaft assembly (434), to further facilitate access to various anatomical passageways. To that end, as shown in FIG. 10, instrument (400) includes shaft rotation assembly (498) for rotating guide shaft assembly (404) about the longitudinal axis (434). Guide shaft assembly (404) rotation can be performed concurrently with deflection control knob (432), if so desired. For example, an operator may require performance of series of guide shaft assembly (404) adjustments, including both rigid shaft member (422) rotation and flexible shaft member (424) deflection to reach the desired anatomical passageway.

As shown in FIGS. 9A-9B, the slotted coupling between slot (492) of pull sleeve (430) and rib (494) of cam barrel (428) permits pull sleeve (430) to operate similarly to a slip coupling, thereby permitting infinite rotation of pull sleeve (430) relative to cam barrel (428), which is fixed in position via rails (488). More specifically, pull sleeve (430) and push-pull wire (426) are capable of rotating 360-degrees without limitation about longitudinal axis (434).

As shown in FIGS. 11A-12B, with additional reference to FIG. 3, shaft rotation assembly (498) is comprised of shaft rotation knob (650) and slotted guide (652). Shaft rotation knob (650) is secured to slotted guide (652) via a slot (654) formed on an outer surface of slotted guide (652). Slot (654) is configured to accept a protrusion (656) on an inner surface of shaft rotation knob (650) such that, as shaft rotation knob (650) is rotated, protrusion (656) corresponds with slot (654) to rotate slotted guide (652) about longitudinal axis (434). Additionally, shaft rotation knob (650) is held into position by pins (658) (FIGS. 9A-9B) securing it to corresponding a rib slot (660) formed around the circumference of housing (464). As shaft rotation knob (650) is rotated, the relationship between pins (658) and rib slot (660) is formed such that pins (658) rotate and translate through rib slot (660), thereby securing shaft rotation knob (650) in position relative to housing (464) while permitting 360-degree rotation of shaft rotation knob (650). Other suitable structures may be used to achieve this relationship between housing (464) and shaft rotation knob (650).

Slotted guide (652) is secured to rigid shaft member (422) and pull sleeve (430), as shown in FIGS. 9A-9B. As described above, pull sleeve (430) and push-pull wire (426) are capable of rotating 360-degrees without limitation about longitudinal axis (434). As such, as shaft rotation knob (650) is rotated, slotted guide (652) is rotated about longitudinal axis (434), resulting in each of pull sleeve (430), push-pull wire (426), and rigid shaft member (422) each similarly rotating about longitudinal axis (434).

Figure 12A:
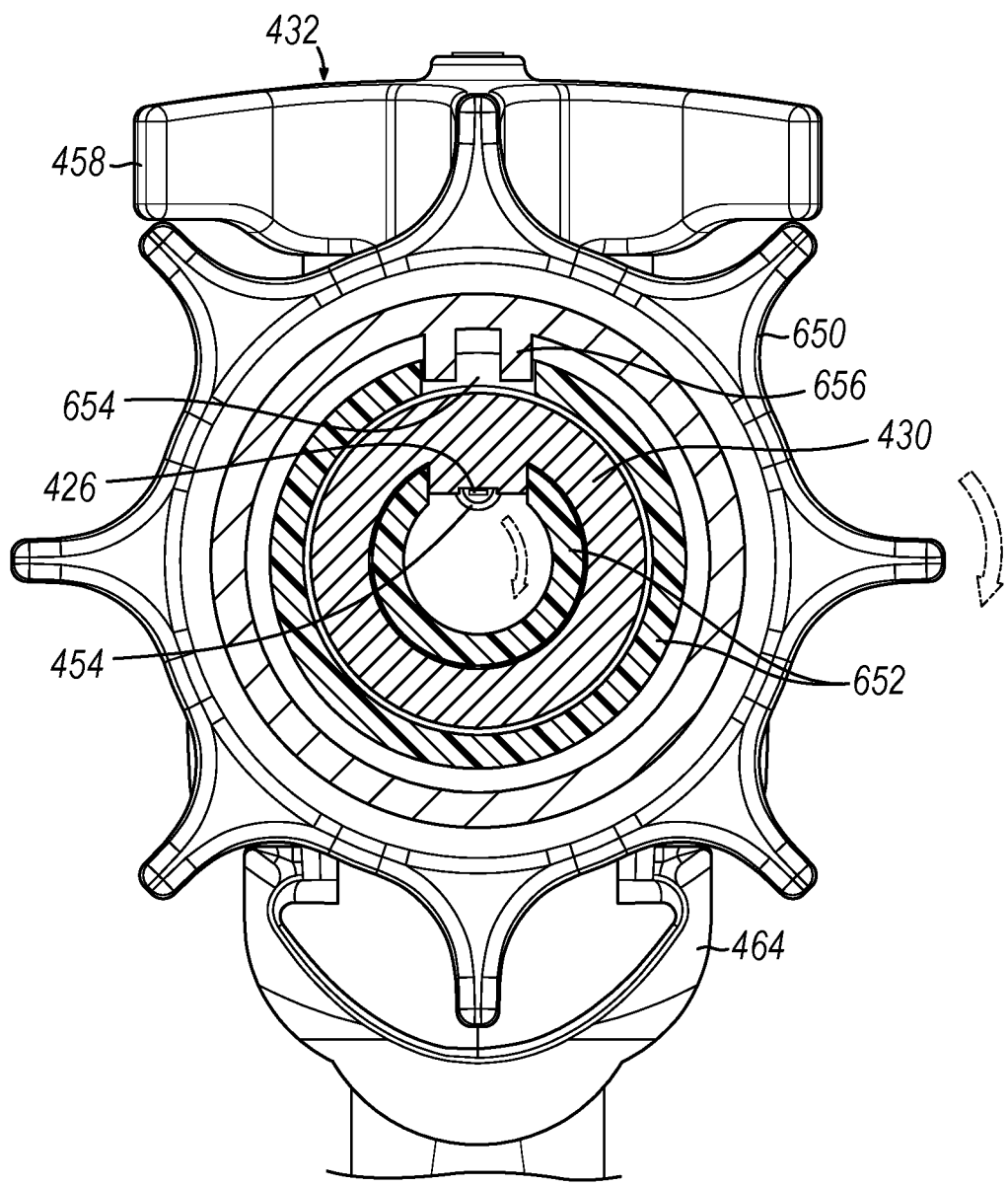
FIG. 12A depicts a cross-sectional view of a portion of the instrument of FIG. 2 taken along line 12-12 of FIG. 10, with the shaft rotation control knob rotated to a first position.
Figure 12B:
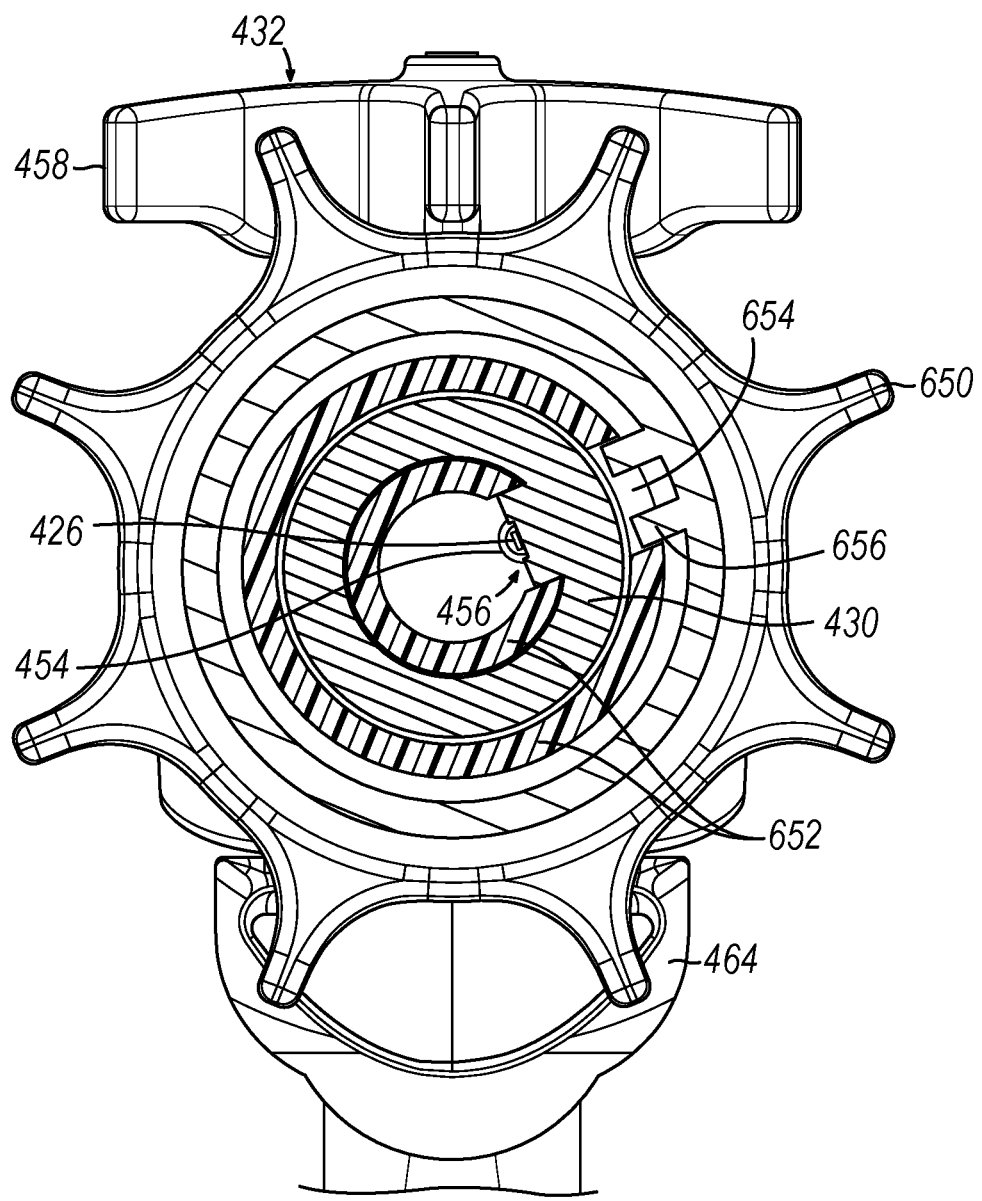
FIG. 12B depicts a cross-sectional view of a portion of the instrument of FIG. 2 taken along line 12-12 of FIG. 10, with the shaft rotation control knob rotated to a second position.

FIGS. 11A and 12A depicts shaft rotation knob (650), and therefore guide shaft assembly (404), in a first rotational position. As shown in FIGS. 11B and 12B, as shaft rotation knob (650) is rotated about longitudinal axis (434), rigid shaft member (422), pull sleeve (430), and push-pull wire (426) are together rotated about longitudinal axis (434).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a shaft assembly extending distally from the body and defining a longitudinal axis, wherein the shaft assembly includes a flexible distal portion; and (c) a deflection actuation assembly, including: (i) a first rotary actuator, (ii) a translatable actuation member extending through the shaft assembly, wherein the translatable actuation member is operatively coupled with the first rotary actuator and the flexible distal portion of the shaft assembly, wherein the first rotary actuator is rotatable by a rotational force to thereby drive the translatable actuation member longitudinally, wherein the flexible distal portion is configured to deflect away from the longitudinal axis in response to translation of the translatable actuation member longitudinally, and (iii) a resilient member positioned between the first rotary actuator and the body, wherein the resilient member is configured to apply a friction force between the first rotary actuator and the body, wherein the friction force is operable to increase the rotational force required to rotate the first rotary actuator.

Example 2

The apparatus of Example 1, wherein the resilient member includes a compression spring.

Example 3

The apparatus of Example 2, wherein the compression spring is formed into a toroidal shape.

Example 4

The apparatus of Example 1, wherein the resilient member includes a garter spring.

Example 5

The apparatus of any of Examples 1-4, wherein the resilient member is configured to radially compress between the first rotary actuator and the body such that the friction force applied between the first rotary actuator and the body is constant.

Example 6

The apparatus of any of Examples 1-5, the first rotary actuator further including a plurality of predefined rotational positions.

Example 7

The apparatus of any of Examples 1-6, further comprising a feedback member coupled with the body and positioned adjacent the first rotary actuator, wherein the feedback member is configured to cooperate with a feedback portion of the first rotary actuator as the first rotary actuator is rotated, wherein the cooperation is operable to produce a feedback indication to a user.

Example 8

The apparatus of Example 7, wherein the feedback indication includes an audible noise.

Example 9

The apparatus of any of Examples 7-8, wherein the feedback indication includes a tactile response.

Example 10

The apparatus of Example 9, wherein the tactile response includes a vibration.

Example 11

The apparatus of any of Examples 7-10, wherein the feedback portion of the first rotary actuator includes one or more detents, wherein the feedback member is configured to contact the one or more detents as the first rotary actuator is rotated.

Example 12

The apparatus of Example 11, wherein each of the one or more detents in the feedback portion of the first rotary actuator is positioned to correspond to a rotational position of the first rotary actuator, wherein the rotational position of the first rotary actuator is configured to correspond to a degree of deflection of the flexible distal portion away from the longitudinal axis.

Example 13

The apparatus of Example 12, wherein the one or more detents includes three detents, wherein the three detents are configured to correspond to 55-degree, 70-degree, and 110-degree deflection angles of the flexible distal portion relative to the longitudinal axis.

Example 14

The apparatus of any of Examples 1-13, further comprising a dilation catheter, wherein the dilation catheter is slidable relative to the shaft assembly, wherein the dilation catheter comprises an expandable dilator.

Example 15

The apparatus of Example 14, further comprising a guidewire, wherein the guidewire is slidably disposed in the dilation catheter.

Example 16

The apparatus of Example 15, further comprising a guidewire actuation assembly, wherein the guidewire actuation assembly is operable to translate the guidewire relative to the body, wherein the guidewire actuation assembly is further operable to rotate the guidewire about the longitudinal axis.

Example 17

The apparatus of any of Examples 1-16, further comprising a shaft rotation assembly, wherein the shaft rotation assembly is operable to rotate the shaft assembly about the longitudinal axis.

Example 18

The apparatus of Example 17, wherein the shaft rotation assembly comprises a second rotary actuator positioned at a distal portion of the body, wherein the second rotary actuator is rotatable about an axis that is perpendicular to the longitudinal axis.

Example 19

The apparatus of any of Examples 1-18, wherein the translatable actuation member includes a pull-wire.

Example 20

The apparatus of any of Examples 1-19, further comprising a pin coupled with the rotary actuator, wherein the rotary actuator is operatively coupled with the translatable actuation member via the pin to drive the translatable actuation member longitudinally.

Example 21

The apparatus of Example 20, wherein the rotary actuator is configured to rotate about a rotary axis, wherein the pin is laterally offset from the rotary axis.

Example 22

The apparatus of any of Examples 20-21, further comprising a slot defined on a surface of the translatable actuation member, wherein the pin is configured to cooperate with the slot to drive the translatable actuation member longitudinally.

Example 23

An apparatus, comprising: (a) a body; (b) a shaft assembly extending distally from the body and defining a longitudinal axis, wherein a portion of the shaft assembly is configured to be inserted into an anatomical passageway of a patient, wherein the shaft assembly includes a flexible distal portion;

and (c) a deflection actuation assembly, including: (i) a translatable actuation member extending through the shaft assembly, wherein the translatable actuation member is operatively coupled with the flexible distal portion, (ii) a rotary actuator, wherein the rotary actuator is rotatable about a rotary axis to thereby actuate the translatable actuation member to deflect the flexible distal portion away from the longitudinal axis, and (iii) a pin coupled with the rotary actuator, wherein the pin is laterally offset from the rotary axis, wherein the rotary actuator is operatively coupled with the translatable actuation member via the pin to actuate the translatable actuation member.

Example 24

The apparatus of Example 23, wherein the rotary axis is oriented transverse to the longitudinal axis.

Example 25

The apparatus of any of Examples 23-24, further comprising a resilient member positioned between the rotary actuator and the body, wherein the resilient member is configured to induce a friction force to partially restrict rotation of the rotary actuator.

Example 26

The apparatus of Example 25, wherein the resilient member includes a compression spring.

Example 27

The apparatus of Example 26, wherein the compression spring is formed into a toroidal shape.

Example 28

The apparatus of any of Examples 23-24, wherein the resilient member includes a garter spring.

Example 29

The apparatus of any of Examples 23-28, wherein the resilient member is configured to radially compress between the rotary actuator and the body such that the friction force applied between the rotary actuator and the body is constant.

Example 30

The apparatus of any of Examples 23-29, further comprising a feedback member coupled with the body and positioned adjacent the rotary actuator, wherein the feedback member is configured to cooperate with a feedback portion of the rotary actuator as the rotary actuator is rotated, wherein the cooperation is operable to produce a tactile feedback indication to a user.

Example 31

The apparatus of Example 30, wherein the feedback indication includes an audible noise.

Example 32

The apparatus of any of Examples 30-31, wherein the feedback indication includes a tactile response.

Example 33

The apparatus of any of Examples 30-32, wherein the feedback portion of the rotary actuator includes one or more detents, wherein the feedback member is configured to contact the one or more detents as the rotary actuator is rotated.

Example 34

The apparatus of Example 33, wherein each of the one or more detents in the feedback portion of the rotary actuator is positioned to correspond to a rotational position of the rotary actuator, wherein the rotational position of the rotary actuator is configured to correspond to a degree of deflection of the flexible distal portion away from the longitudinal axis.

Example 35

The apparatus of any of Examples 33-34, wherein the one or more detents includes three detents, wherein the three detents are configured to correspond to 55-degree, 70-degree, and 110-degree deflection angles of the flexible distal portion relative to the longitudinal axis.

Example 36

An apparatus, comprising: (a) a body; (b) a shaft assembly extending distally from the body and defining a longitudinal axis, wherein a portion of the shaft assembly is configured to be inserted into an anatomical passageway of a patient, wherein the shaft assembly includes a flexible distal portion; (c) a deflection actuation assembly operatively coupled with the flexible distal portion of the shaft assembly, wherein a rotary actuator is rotatable about a rotary axis to thereby deflect the flexible distal portion away from the longitudinal axis, wherein the rotary axis is transverse to the longitudinal axis of the shaft assembly; and (d) a feedback member coupled with the body and positioned adjacent the rotary actuator, wherein the feedback member is configured to cooperate with a feedback portion of the rotary actuator as the rotary actuator is rotated, wherein the cooperation is operable to produce a feedback indication to a user.

Example 37

The apparatus of Example 36, wherein the rotary axis is perpendicular to the longitudinal axis of the shaft assembly.

Example 38

The apparatus of any of Examples 36-37, wherein the feedback indication includes an audible noise.

Example 39

The apparatus of any of Examples 36-38, wherein the feedback indication includes a tactile response.

Example 40

The apparatus of Example 39, wherein the tactile response includes a vibration.

Example 41

The apparatus of any of Examples 36-40, wherein the feedback portion of the rotary actuator includes one or more detents, wherein the feedback member is configured to contact the one or more detents as the first rotary actuator is rotated.

Example 42

The apparatus of Example 41, wherein each of the one or more detents in the feedback portion of the first rotary actuator is positioned to correspond to a rotational position of the first rotary actuator, wherein the rotational position of the first rotary actuator is configured to correspond to a degree of deflection of the flexible distal portion away from the longitudinal axis.

Example 43

The apparatus of Example 42, wherein the one or more detents includes three detents, wherein the three detents are configured to correspond to 55-degree, 70-degree, and 110-degree deflection angles of the flexible distal portion relative to the longitudinal axis.

Example 44

The apparatus of any of Examples 36-43, further comprising a resilient member positioned between the rotary actuator and the body, wherein the resilient member is configured to radially compress between the rotary actuator and the body, wherein the resilient member is operable to induce a constant friction force to partially restrict rotation of the rotary actuator.

Example 45

The apparatus of Example 44, wherein the resilient member includes a compression spring.

Example 46

The apparatus of Example 45, wherein the compression spring is formed into a toroidal shape.

Example 47

The apparatus of Example 44, wherein the resilient member includes a garter spring.

Example 48

The apparatus of any of Examples 44-47, wherein the resilient member is configured to radially compress between the first rotary actuator and the body such that the friction force applied between the first rotary actuator and the body is constant.

Example 49

The apparatus of any of Examples 36-48, further comprising a pin coupled with the rotary actuator, wherein the rotary actuator is operatively coupled with the translatable actuation member via the pin to drive the translatable actuation member longitudinally.

Example 50

The apparatus of Example 49, wherein the rotary actuator is configured to rotate about a rotary axis, wherein the pin is laterally offset from the rotary axis.

Example 51

The apparatus of any of Examples 49-50, further comprising a slot defined on a surface of the translatable actuation member, wherein the pin is configured to cooperate with the slot to drive the translatable actuation member longitudinally.

Example 52

An apparatus, comprising: (a) a body; (b) a shaft assembly extending distally from the body and defining a longitudinal axis, wherein the shaft assembly includes a flexible distal portion; and (c) a deflection actuation assembly, including: (i) a first rotary actuator, (ii) a cam member, wherein the first rotary actuator is rotatable to translate the cam member longitudinally along the longitudinal axis relative to the body, (iii) a pull member slidably coupled with the cam member, wherein the cam member is longitudinally translatable to translate the pull member longitudinally, wherein the pull member is configured to rotate about the longitudinal axis relative to the body and relative to the cam member, and (iv) a translatable actuation member coupled with the pull member and the flexible distal portion of the shaft assembly, wherein the flexible distal portion is configured to deflect away from the longitudinal axis in response to translation of the translatable actuation member longitudinally.

Example 53

The apparatus of Example 52, further comprising a pin coupled with the first rotary actuator, wherein the first rotary actuator is operatively coupled with the translatable actuation member via the pin to drive the translatable actuation member longitudinally.

Example 54

The apparatus of Example 53, wherein the first rotary actuator is configured to rotate about a rotary axis, wherein the pin is laterally offset from the rotary axis.

Example 55

The apparatus of any of Examples 53-54, further comprising a slot defined on a surface of the translatable actuation member, wherein the pin is configured to cooperate with the slot to drive the translatable actuation member longitudinally.

Example 56

The apparatus of Example 55, wherein the slot has a linear configuration.

Example 57

The apparatus of any of Examples 52-56, wherein the pull member and the cam member couple together via a rib-slot coupling.

Example 58

The apparatus of any of Examples 52-57, wherein the pull member is rotatable about the longitudinal axis to rotate the shaft assembly about the longitudinal axis.

Example 59

The apparatus of any of Examples 52-58, wherein the translatable actuation member is coaxially and slidably disposed about the shaft assembly.

Example 60

The apparatus of any of Examples 52-59, wherein the cam member and body include complementary features permitting the cam member to translate longitudinally relative to the body while preventing the cam member from rotating about the longitudinal axis.

Example 61

The apparatus of any of Examples 52-60, further comprising a shaft rotation assembly, wherein the shaft rotation assembly is operable to rotate the shaft assembly about the longitudinal axis.

Example 62

The apparatus of Example 61, wherein the shaft rotation assembly comprises a second rotary actuator positioned at a distal portion of the body, wherein the second rotary actuator is rotatable about the longitudinal axis.

Example 63

The apparatus of Example 62, wherein the first rotary actuator and the second rotary actuator are each actuatable by a hand of a user grasping the body without requiring the user to reposition the hand.

Example 64

The apparatus of any of Examples 52-63, wherein the translatable actuation member includes a pull-wire.

Example 65

The apparatus of any of Examples 52-64, further comprising a dilation catheter, wherein the dilation catheter is slidable relative to the shaft assembly, wherein the dilation catheter comprises an expandable dilator.

Example 66

The apparatus of any of Examples 52-65, further comprising a guidewire, wherein the guidewire is slidably disposed in the dilation catheter.

Example 67

The apparatus of any of Examples 52-66, wherein the flexible distal portion of the shaft assembly is concurrently operable to deflect away from the longitudinal axis while the shaft assembly rotates about the longitudinal axis.

Example 68

The apparatus of any of Examples 52-67, further comprising a feedback member coupled with the body and positioned adjacent the first rotary actuator, wherein the feedback member is configured to cooperate with a feedback portion of the first rotary actuator as the first rotary actuator is rotated, wherein the cooperation is operable to produce a feedback indication to a user.

Example 69

The apparatus of Example 68, wherein the feedback indication includes at least one of an audible noise and a tactile response.

Example 70

The apparatus of any of Examples 68-69, wherein the feedback portion of the first rotary actuator includes one or more detents, wherein the feedback member is configured to contact the one or more detents as the first rotary actuator is rotated.

Example 71

The apparatus of any of Examples 52-70, where the translatable actuation member is laterally offset from the longitudinal axis.

Example 72

An apparatus, comprising: (a) a body; (b) a shaft assembly extending distally from the body and defining a longitudinal axis, wherein the shaft assembly includes a flexible distal portion; (c) a deflection actuation assembly, including: (i) a first rotary actuator, (ii) a cam member, wherein the first rotary actuator is rotatable to translate the cam member distally and proximally relative to the body, (iii) a pull member coupled with the cam member, wherein the cam member is longitudinally translatable to translate the pull member distally and proximally, wherein the pull member is configured to rotate about the longitudinal axis, and (iv) a translatable actuation member coupled with the pull member and the flexible distal portion of the shaft assembly; and (d) a shaft rotation assembly, wherein the shaft rotation assembly is operable to rotate the shaft assembly and the pull member about the longitudinal axis.

Example 73

The apparatus of Example 72, further comprising a pin coupled with the first rotary actuator, wherein the first rotary actuator is operatively coupled with the translatable actuation member via the pin to drive the translatable actuation member longitudinally.

Example 74

The apparatus of Example 73, wherein the first rotary actuator is configured to rotate about a rotary axis, wherein the pin is laterally offset from the rotary axis.

Example 75

The apparatus of any of Examples 73-74, further comprising a slot defined on a surface of the translatable actuation member, wherein the pin is configured to cooperate with the slot to drive the translatable actuation member longitudinally.

Example 76

The apparatus of any of Examples 75, wherein the slot has a linear configuration.

Example 77

The apparatus of any of Examples 72-76, wherein the pull member and the cam member couple together using a rib-slot coupling.

Example 78

The apparatus of any of Examples 72-77, wherein a rotation of the pull member about the longitudinal axis is operable to rotate the shaft assembly about the longitudinal axis.

Example 79

The apparatus of any of Examples 72-78, wherein the cam member and body include complementary features permitting the cam member to translate longitudinally relative to the body while preventing the cam member from rotating about the longitudinal axis.

Example 80

The apparatus of any of Examples 72-79, further comprising a shaft rotation assembly, wherein the shaft rotation assembly is operable to rotate the shaft assembly about the longitudinal axis.

Example 81

The apparatus of Example 80, wherein the shaft rotation assembly comprises a second rotary actuator positioned at a distal portion of the body, wherein the second rotary actuator is rotatable about an axis that is perpendicular to the longitudinal axis.

Example 82

The apparatus of Example 81, wherein the first rotary actuator and the second rotary actuator are each actuatable by a hand of a user without requiring the user to reposition the hand.

Example 83

The apparatus of any of Examples 72-82, wherein the translatable actuation member includes a pull-wire.

Example 84

The apparatus of any of Examples 72-83, further comprising a dilation catheter, wherein the dilation catheter is slidable relative to the shaft assembly, wherein the dilation catheter comprises an expandable dilator.

Example 85

The apparatus of any of Examples 72-84, wherein the flexible distal portion of the shaft assembly is concurrently operable to deflect away from the longitudinal axis while the shaft assembly rotates about the longitudinal axis.

Example 86

An apparatus, comprising: (a) a body; (b) a shaft assembly extending distally from the body and defining a longitudinal axis, (c) a shaft rotation assembly, wherein the shaft rotation assembly is operable to rotate the shaft assembly about the longitudinal axis, and (d) a deflection actuation assembly, including: (i) a rotary actuator, (ii) a cam member, wherein a rotation of the rotary actuator is operable to translate the cam member distally and proximally relative to the body, (iii) a pull member coupled with the cam member via a slip coupling, wherein the rotary actuator is rotatable to translate the pull member longitudinally, wherein the pull member is configured to rotate about the longitudinal axis relative to the cam member in response to a rotation of the shaft rotation assembly about the longitudinal axis, and (iv) a translatable actuation member coupled with the pull member, wherein the translatable actuation member is configured to deflect a portion of the shaft assembly away from the longitudinal axis in response to translation of the translatable actuation member longitudinally.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body that includes an actuation assembly slidably coupled with the body;
   (b) a shaft assembly extending distally from the body and defining a longitudinal axis, the shaft assembly including a flexible distal portion, the actuation assembly being configured to translate along the body to distally advance one of a guidewire or a dilation catheter relative to the shaft assembly; and
   (c) a deflection actuation assembly, including:
      (i) a first rotary actuator,
      (ii) a translatable actuation member extending through the shaft assembly, the translatable actuation member being operatively coupled with the first rotary actuator and the flexible distal portion of the shaft assembly, the first rotary actuator being rotatable by a rotational force to thereby drive the translatable actuation member longitudinally, the flexible distal portion being configured to deflect away from the longitudinal axis in response to translation of the translatable actuation member longitudinally, and
      (iii) a resilient member positioned between the first rotary actuator and the body, the resilient member being configured to apply a friction force between the first rotary actuator and the body, the friction force being operable to increase the rotational force required to rotate the first rotary actuator.

2. The apparatus of claim 1, the resilient member including a compression spring.

3. The apparatus of claim 2, the compression spring being formed into a toroidal shape.

4. The apparatus of claim 1, the resilient member including a garter spring.

5. The apparatus of claim 1, the resilient member being configured to radially compress between the first rotary actuator and the body such that the friction force applied between the first rotary actuator and the body is constant.

6. The apparatus of claim 1, the first rotary actuator further including a plurality of predefined rotational positions.

7. The apparatus of claim 1, further comprising a feedback member coupled with the body and positioned adjacent the first rotary actuator, the feedback member being configured to cooperate with a feedback portion of the first rotary actuator as the first rotary actuator is rotated, the cooperation being operable to produce a feedback indication to a user.

8. The apparatus of claim 7, the feedback portion of the first rotary actuator including one or more detents, the feedback member being configured to contact the one or more detents as the first rotary actuator is being rotated.

9. The apparatus of claim 8, each of the one or more detents in the feedback portion of the first rotary actuator being positioned to correspond to a rotational position of the first rotary actuator, the rotational position of the first rotary actuator being configured to correspond to a degree of deflection of the flexible distal portion away from the longitudinal axis.

10. The apparatus of claim 1, further comprising the dilation catheter, the dilation catheter being slidable relative to the shaft assembly, the dilation catheter comprising an expandable dilator.

11. The apparatus of claim 10, further comprising the guidewire, the guidewire being slidably disposed in the dilation catheter.

12. The apparatus of claim 1, further comprising a shaft rotation assembly, the shaft rotation assembly being operable to rotate the shaft assembly about the longitudinal axis, the shaft rotation assembly comprising a second rotary actuator positioned at a distal portion of the body, the second rotary actuator being rotatable about the longitudinal axis.

13. The apparatus of claim 1, further comprising a pin coupled with the rotary actuator, the rotary actuator being operatively coupled with the translatable actuation member via the pin to drive the translatable actuation member longitudinally, the rotary actuator being configured to rotate about a rotary axis, the pin being laterally offset from the rotary axis.

14. The apparatus of claim 1, the resilient member defining a long axis and a short axis, the short axis being perpendicular to the long axis and the longitudinal axis.

15. The apparatus of claim 1, the first rotary actuator including a deflection control knob and a body, the resilient member being positioned between the deflection control knob and the body.

16. An apparatus, comprising:
   (a) a body;
   (b) a shaft assembly extending distally from the body and defining a longitudinal axis, a portion of the shaft assembly being configured to be inserted into an anatomical passageway of a patient, the shaft assembly comprising:
      (i) a rigid proximal portion, and
      (ii) a flexible distal portion;
   (c) a deflection actuation assembly operatively coupled with the flexible distal portion of the shaft assembly, a rotary actuator rotatable about a rotary axis to thereby deflect the flexible distal portion away from the longitudinal axis without deflecting the rigid proximal portion, the rotary axis being transverse to the longitudinal axis of the shaft assembly; and (d) a feedback member coupled with the body and positioned adjacent the rotary actuator, the feedback member being configured to cooperate with a feedback portion of the rotary actuator as the rotary actuator is being rotated, the cooperation being operable to produce a feedback indication to a user.

17. The apparatus of claim 16, the rotary axis being perpendicular to the longitudinal axis of the shaft assembly.

18. The apparatus of claim 16, the feedback portion of the rotary actuator including one or more detents, the feedback member being configured to contact the one or more detents as the first rotary actuator is rotated.

19. The apparatus of claim 18, each of the one or more detents in the feedback portion of the first rotary actuator being positioned to correspond to a rotational position of the first rotary actuator, the rotational position of the first rotary actuator being configured to correspond to a degree of deflection of the flexible distal portion away from the longitudinal axis.

20. An apparatus, comprising:
(a) a body;
(b) a shaft assembly extending distally from the body and defining a longitudinal axis, the shaft assembly including a flexible distal portion; and
(c) a deflection actuation assembly, including:
 (i) a first rotary actuator rotatable about a rotary plane that is parallel and offset from the longitudinal axis,
 (ii) a cam member, the first rotary actuator being rotatable to translate the cam member longitudinally along the longitudinal axis relative to the body,
 (iii) a pull member slidably coupled with the cam member, the cam member being longitudinally translatable to translate the pull member longitudinally, the pull member being configured to rotate about the longitudinal axis relative to the body and relative to the cam member, and
 (iv) a translatable actuation member coupled with the pull member and the flexible distal portion of the shaft assembly, the flexible distal portion being configured to deflect away from the longitudinal axis in response to translation of the translatable actuation member longitudinally.

* * * * *